United States Patent [19]

Barsov et al.

[11] Patent Number: 6,096,534
[45] Date of Patent: Aug. 1, 2000

[54] RETROVIRUS VECTORS DERIVED FROM AVIAN SARCOMA LEUKOSIS VIRUSES PERMITTING TRANSFER OF GENES INTO MAMMALIAN CELLS

[75] Inventors: Eugene Barsov, Frederick; Stephen H. Hughes, Smithsburg, both of Md.

[73] Assignee: The United States of America as represented by the Department of Health and Human Services, Washington, D.C.

[21] Appl. No.: 08/875,509

[22] PCT Filed: May 22, 1996

[86] PCT No.: PCT/US96/07370

§ 371 Date: Nov. 28, 1997

§ 102(e) Date: Nov. 28, 1997

[87] PCT Pub. No.: WO96/37625

PCT Pub. Date: Nov. 28, 1996

Related U.S. Application Data

[63] Continuation-in-part of application No. 08/445,462, May 22, 1995, abandoned.

[51] Int. Cl.$^7$ .............................. C12N 15/00; C12N 7/00; C12N 5/10
[52] U.S. Cl. .................................. 435/320.1; 435/235.1; 435/325
[58] Field of Search ............................ 435/320.1, 235.1, 435/325; 424/93.1, 93.21; 514/44

[56] References Cited

U.S. PATENT DOCUMENTS

| | | | |
|---|---|---|---|
| 4,861,719 | 8/1989 | Miller | 435/236 |
| 4,997,763 | 3/1991 | Hughes et al. | 800/23 |
| 5,124,263 | 6/1992 | Temin et al. | 435/349 |

OTHER PUBLICATIONS

Verma et al. (1997) Nature, vol. 389, 239–242, Sep. 1997.
F. D. Ledley (1991) Human Gene Therapy, vol. 2, 77–83, 1991.
T. Friedmann (1997) Scientific American, vol., 96–101, Jun. 1997.
Orkin et al. (1995) "Report and Recommendations of the Panel to Assess the NIH Investment in Research on Gene Therapy", Dec. 1995.
Otto et al., "Characterization Of A Replication–Competent Retrovirus Resulting From Recombination Of Packaging And Vector Sequences" (1994) *Human Gene Ther.* 5:567–575.
Hughes and Kosik, "Mutagenesis Of The Region Between env and src Of The SR–A Strain of Rous Sarcoma Virus For the Purpose of Constructing Helper–Independent Vectors" (1984) *J. Virology* 136:89–99.
Hughes et al., "Adaptor Plasmids Simplify the Insertion of Foreign DAN Into Helper–Independent Retroviral Vectors" (1987) *J. Virology* 61:3004–3012.
Greenhouse et al., "Helper–Independent Retrovirus Vectors with Rous–Associated Virus Type O Long Terminal Repeats"(1988) *J. Virology* 62:4809–4812.
Hughes and Kosik, "Design of Retroviral Vectors For The Insertion of Foreign Deoxyribonucleic Acid Sequences Into The Avian Germ Line" (1986) *Poult. Sci.* 65:1459–1467.
Petropoulos and Hughes, "Replication—Competent Retrovirus Vectors For The Transfer And Expression of Gene Cassettes In Avian Cells" (1991) *J. Virology* 65:3728–3737.
Petropoulos et al., "Appropriate In Vivo Expression of A Muscle Specific Promoter By Using Avian Retroviral Vectors For Gene Transfer" (1992) *J. Virology* 66:3391–3397.
Salter et al., "Gene Insertion Into The Chicken Germ Line By Retroviruses" (1986) *Poult. Sci.* 65:1445–1458.
Salter et al. "Transgenic Chickens: Insertion of Retroviral Genes Into The Check Germ Line" (1987) *J. Virology* 157:236–240.
Valsessia–Wittman et al., "Modifications In The Binding Domain of Avian Retrovirus Envelope Protein To Redirect The Host Range of Retroviral Vectors" (1994) *J. Virology* 68:4609–4619.
Federspiel et al., "A System For Tissue–Specific Gene Targeting:Transgenic Mice Susceptible To Subgroup A Avian Leukosis Virus–Based Retroviral Vectors" (1994) *PNAS* (U.S.A.) 91:11241–11245.
Weiss and Wong "Phenotypic Mixing Between Avian and Mammalian RNA Tumor Viruses: I. Envelope Pseudotypes of Rous Sarcoma Virus" (1977) *J. Virology* 76:826–834.
Weiss et al., "Pseudotypes of Avian Sarcoma Viruses With The Envelope Properties of Vesicular Stomatitis Virus" (1977) *J. Virology* 76–808–825.
Emi et al., "Pseudotype Formation of Murine Leukemia Virus With The G Protein Of Vesicular Stomatitis Virus" (1991) *J. Virology* 65:1202–1207.
Burns et al., "Vesicular Stomatitis Virus G Glycoprotein Pseudotyped Retroviral Vectors: Concentration To Very High Titer and Efficient Gene Transfer Into Mammalian And Nonmammalian Cells" (1993) *PNAS* (U.S.A.) 90:8033–8037.
Hopkins, "High Titers Of Retrovirus (Vesicular Stomatitis Virus) Pseudotypes, At Last" (1993) *PNAS* (U.S.A.) 90:8759–8760.
Dong et al., "A Chimeric Avian Retrovirus Containing The Influenza Virus Hemagglutinin Gene Has An Expanded Hoot Range" (1992) *J. Virology* 66:7374–7382.
Landau and Littman, "Packaging System For Rapid Production Of Murine Leukemia Virus Vectors With Variable Tropism" (1992) *J. Virology* 66:5110–5113.
Ott et al., "Sequence Analysis of Amphotropic and 10A1 Murine Leukemia Viruses: Close Relationship To Mink Cell Focus–Inducing Viruses" (1990) *J. Virology* 64:757–766.
Ott and Rein et al., "Basis For Receptor Specificity Of Nonecotropic Murine Leukemia Virus Surface Glycoprotein gp70$^{su}$" (1992) *J. Virology* 66:4632–4638.

*Primary Examiner*—Karen M. Hauda
*Assistant Examiner*—Anne Marie S. Beckerleg
*Attorney, Agent, or Firm*—Morgan & Finnegan, L.L.P.; William S. Feiler; Dorothy R. Auth

[57] ABSTRACT

Recombinant avian sarcoma leukosis virus (ASLV)-derived retrovirus vectors having an expanded host range are described. The host range is expanded by the replacement of the ASLV envelope gene by an envelope gene from a virus capable of infecting both mammalian and avian cells. The resulting recombinant ASLV-derived retroviral vectors can replicate efficiently in avian cells, infect both avian and mammalian cells in high titer, and are replication-defective in mammalian cells. Thus, they are quite safe and advantageous for use in gene therapy and vaccines.

18 Claims, 12 Drawing Sheets

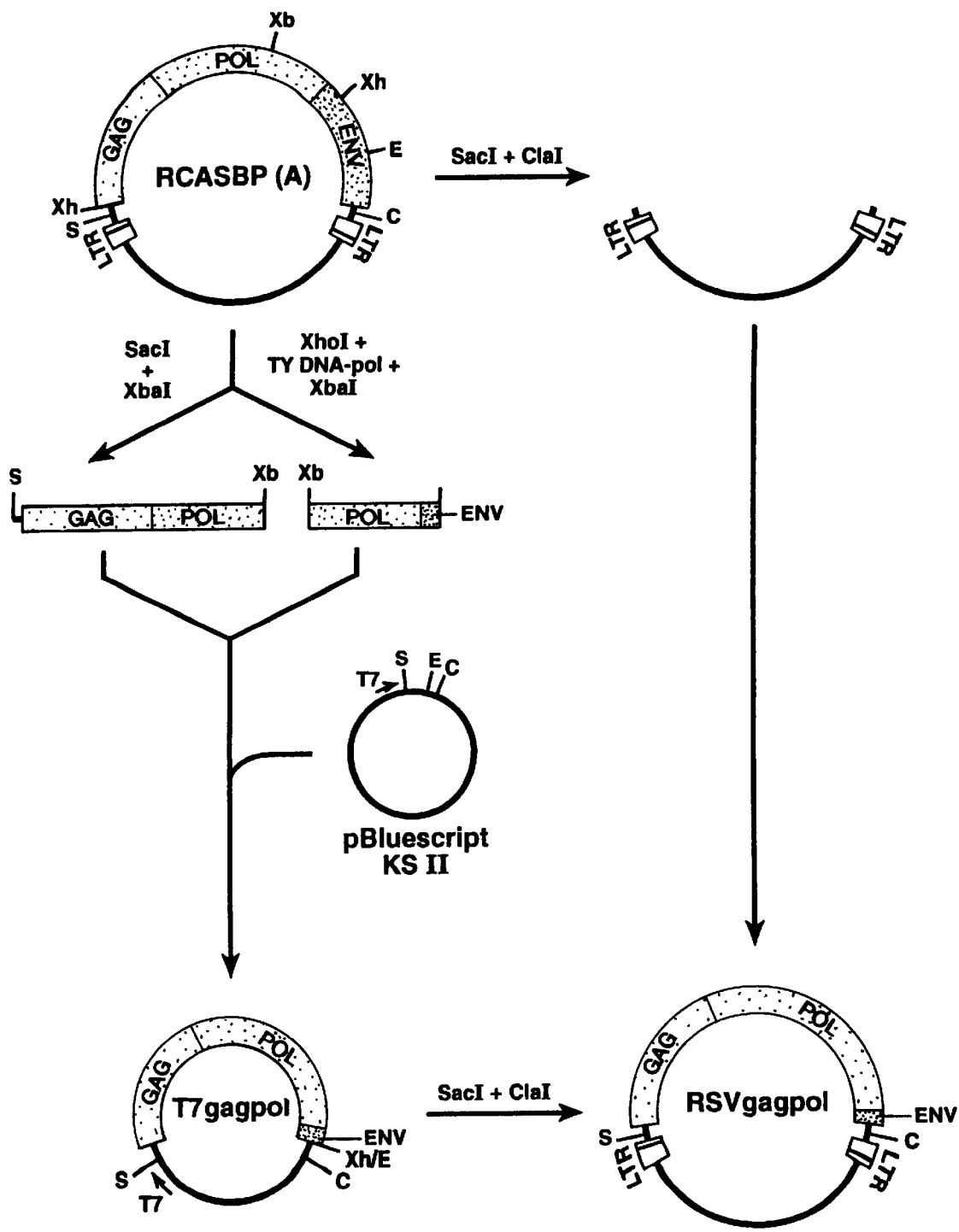
FIG.IA

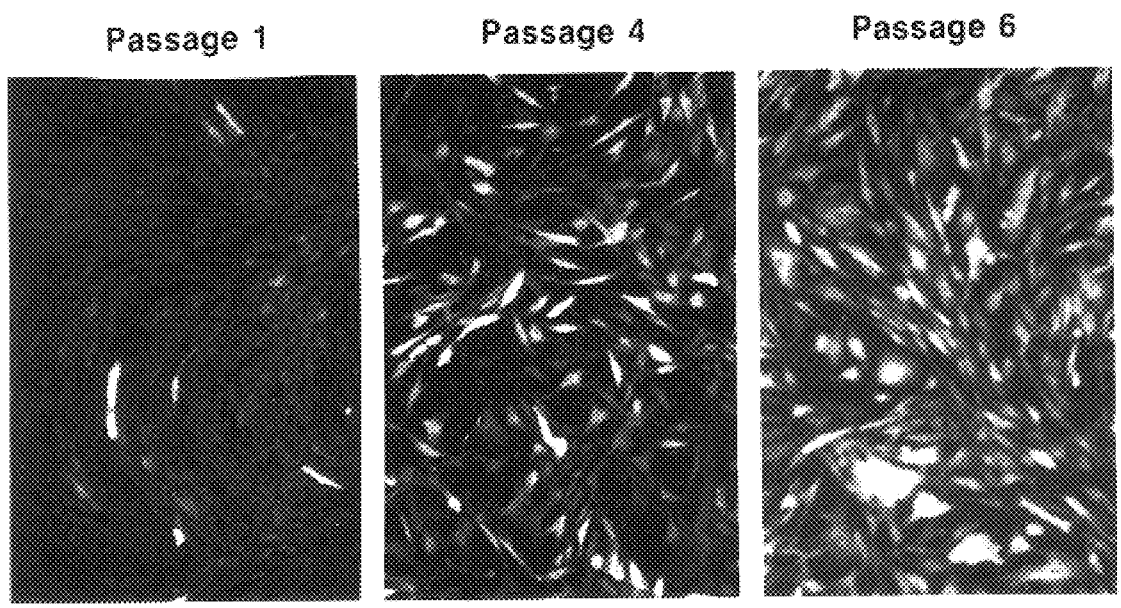
FIG.4A
FIG.4B
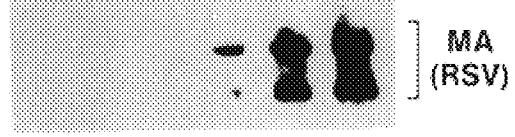

RETROVIRUS VECTORS DERIVED FROM AVIAN SARCOMA LEUKOSIS VIRUSES PERMITTING TRANSFER OF GENES INTO MAMMALIAN CELLS

CROSS-REFERENCE TO RELATED APPLICATIONS

This application is a continuation-in-part of U.S. patent application Ser. No. 08/445,462, filed May 22, 1995, now abandoned.

FIELD OF INVENTION

This invention relates to the fields of genetic engineering and gene transfer. More specifically, the invention relates to recombinant retrovirus vectors derived from avian sarcoma leukosis viruses (ASLVs) having an expanded host range. In particular, this invention relates to ASLV recombinant retrovirus vectors wherein a viral env gene derived from a virus capable of infecting both mammalian and avian cells is substituted for the ASLV env gene, allowing the vectors to efficiently infect a wide range of host cells, including mammalian and particularly human cells, in high titers. Additionally, this invention encompasses therapeutic applications employing these vectors.

BACKGROUND OF INVENTION

Retroviral vectors carrying and expressing nucleic acid sequences of interest are powerful tools for the transfer of genes into a broad range of mammalian cells and into animals, including humans. Indeed, retroviruses offer substantial advantages for use as vectors carrying and expressing desired nucleic acid sequences in both cultured cells and intact animals. (Weiss et al, *RNA Tumor Viruses* (1982)).

First, the retrovirus life cycle lends itself to the efficient transfer of genes into host cells. The infectious retroviral agent is called a viral particle or a virion. Virions consist of a capsid containing the viral genome and any inserted nucleic acid sequences and an envelope made up of glycoproteins. The envelope glycoproteins on the surface of the virion recognize receptors on the host cell that mediate entry of the RNA retroviral genome into the host cell. Once inside the host cell, a double stranded DNA copy of the virion RNA genome and any inserted nucleic acid sequences of interest is made by a viral enzyme, reverse transcriptase. This DNA copy integrates into the host genome at a precise point on the viral DNA molecule and at random, or nearly random sites on host chromosonal DNA. The integrated viral DNA copy is called a provirus. Since a DNA copy of the viral genome integrates into the host genome, the progeny of a single infected host cell are all infected, and the provirus is located in the same place in the genome of each of the progeny cells.

Second, in completing their replicative process, retroviruses usually do not lyse the host cell. Thus, the retroviruses constitute an efficient mechanism for the introduction and high level expression of genes in living host cells.

Third, retroviral genomes are small, making it relatively easy to manipulate a cloned DNA copy of the genome. Moreover, the viruses are efficient; in culture, essentially all of the cells can be infected.

The ability of the retroviral replication machinery to introduce genetic information into the genome of the target cell provided the inspiration for the development of recombinant retrovirus vectors containing a nucleic acid sequence of interest as a vehicle for the stable transfer of genes. Moreover, recombinant retroviral vectors have been used in a number of applications in addition to the expression of genes of interest, including insertional mutagenesis, cell lineage studies and the creation of transgenic animals.

A desirable property useful for the retroviral vector is the ability to replicate in certain easily manipulated host cells, (e.g., avian cells) allowing rapid replication in these cells without aid of a helper or packaging cell line. This permits generation of high titer virus stocks by simply passaging transfected cells and allowing the virus to spread.

Another useful property for a retroviral vector is the ability to infect a wide range of host cells, including mammalian, and particularly human, cells in high titers. Preferably, the retroviral vector is unable to replicate in mammalian cells. Thus, once the vector enters the mammalian host cell, it becomes a stable provirus, integrated in the host cell genome and incapable of further rounds of infection in either the present or subsequent generations.

A number of retroviral vector systems have been described, including systems based on both mammalian (murine leukemia virus, Cepko, et al., (1984) *Cell* 37:1053–1062, Cone and Mulligan, (1984) *PNAS* (U.S.A.) 81:6349–6353; mouse mammary tumor virus, Salmons et al., (1984) *Biochem. Biophys. Res. Commun.* 159:1191–1198; gibbon ape leukemia virus, Miller et al. (1991) *J. Virology,* 65:2220–2224; human immunodeficiency virus, Buchschacher and Panganiban, (1992) *J. Virology* 66:2731–2739, Page et al., (1990) *J. Virology* 64:5270–5276) Shimada et al., (1991) *J. Clin. Invest.* 88:1043–1047); and avian retroviruses (Boerkoel et al., (1993) *Virology* 195:669–679, Cosset et al., (1990) *J. Virology* 64:1070–1078, Greenhouse et al., (1988) *J. Virology* 62:4809–4812, Hughes et al., (1986) *Poult. Sci.* 65:1459–1467, Petropoulos and Hughes, (1991) *J. Virology* 65:3728–3737, Valsessia et al., (1992) *J. Virology* 66:5671–5676). However, none of these vector systems combines all of the above features. Indeed, each of the available retroviral vectors suffers from certain disadvantages.

For example, one of the most widely used retroviral vectors is a replication-defective derivative of Moloney murine leukemia virus (MLV). The main advantage of MLV is that it has a wide host range and can infect mammalian host cells, including human cells. However, the vectors derived from this virus are replication-defective. MLV vectors contain all of the cis-active elements necessary for viral replication, but lack the genes for the viral structural proteins. These proteins must be provided in trans by a helper or packaging cell line.

MLV and other replication-defective vectors have two major disadvantages. First, the titers of recombinant retrovirus produced by a helper or packaging cell line are not always sufficient for some applications, for example, for in vivo gene transfer experiments or gene therapy. (See, e.g. Hopkins, (1993) *PNAS* (U.S.A.) 90:8759–8760). Second, recombination events between the helper or packaging cell line genome and the replication-defective vector can occur and can result in the generation of wild-type virus. (Ott et al., (1994) *Hum. Gene Ther.* 5:567–575). Contamination of the recombinant retroviral vector stock with replication-competent MLV can interfere with gene transfer and present potentially serious problems if the vector is used for gene therapy. For example, leukemias and lymphomas were induced in primates infected by the wild-type MLV contaminating retroviral vector stocks. (Donahue et al., (1992) *J. Exp. Med.* 176:1125–1135; Vanin et al., (1994) *J. Virology* 68:4241–4250). Finally, in order to use a helper or packaging cell line, a selectable marker must be introduced into the retroviral vector. However, with a helper-independent system there is no need to introduce a selectable marker into the vector, since any sequence present in the vector will be carried along passively during replicants.

Other frequently used retroviral vectors are derived from avian sarcoma leukosis viruses (ASLVs), particularly the Rous sarcoma virus (RSV). (Hughes and Kosik (1984) *Virology* 136:89–99; Hughes et al., (1987) *J. Virology* 61:3004–3012). RSV is the only known replication-competent retrovirus carrying an additional gene, oncogene v-src, which is dispensable for viral replication. This oncogene can be deleted from the RSV derived vector and replaced with a gene or genes of interest without affecting the ability of the virus to replicate. For example, retroviral vectors derived from RSV in which the v-src sequences present in the parental RSV have been replaced with a unique restriction site, Cla I, which can be used to insert the gene or genes of interest have previously been described. These vectors are designated the RCAS series. (Hughes et al., (1987) *J. Virology* 61:3004–3102). The stability of these vectors was improved by removal of the direct repeat upstream of the src region. (Hughes et al., (1987) *J. Virology* 61:3004–3102). The construction and advantages of these vectors are described in Petropoulos and Hughes (1991) *J. Virology* 65:3728–3737. (See also Hughes and Kosik (1984) *Virology* 136:89–99). Retrovirus vectors derived from replication competent endogenous Rous associated virus type-O (RAV-O) are designated RCOS (Greenhouse, et al., (1988) *J. Virology* 62:4809–4812). Vectors without splice acceptors are designated RCON and RCAN. (Hughes et al., U.S. Pat. No. 4,997,763 (filed Jul. 31, 1987, issued Mar. 5, 1991), Hughes et al., (1987) *J. Virology* 61:3004–3012, Petropoulos and Hughes, (1991). *J. Virology* 65:3728–3737, Greenhouse, et al., (1988) *J. Virology* 62:4809–4812).

In contrast to the replication-defective vectors, recombinant retrovirus vectors based on RSV or other replication competent ASLVs do not require a packaging or helper cell line. Thus, these vectors can replicate in avian cells without the assistance of helper or packaging cell lines. Consequently, high-titer viral stocks may be easily prepared by transfecting a plasmid containing the vector into cultured chicken embryo fibroblasts (CEFS) or other avian cells, and passaging the transfected cells and allowing the virus to spread. The simplicity of the virus stock preparation and the high titers that are easily achievable with the replication-competent retroviral vectors are significant advantages. Additionally, these vectors have the desirable property of being unable to replicate in mammalian cells. (Federspiel et al., (1994) *PNAS* (U.S.A.) 91:11241–11245). RSV-derived RCAS vectors have been used to express a number of genes and to make transgenic chickens. (Hughes et al., (1990) *J. Reprod. Fertil. Suppl.* 41:39–49; Petropoulos and Hughes, (1991) *J. Virology* 65:3728–3737; Petropoulos et al., (1992) *J. Virology* 66:3391–3397; Salter et al., (1986) *Poult. Sci.* 65:1445–1458; Salter et al., (1987) *Virology* 157:236–240).

An important limitation of RSV and other ASLV-based vectors is their host range. The ASLV-derived vectors disclosed prior to the instant invention could not efficiently infect mammalian cells. In order to infect a host cell, the envelope (env) glycoprotein of a retrovirus must specifically bind to a cognate receptor on the surface of the host cell. Thus, host range is defined by the binding capability of the env glycoprotein. In RSV and other ASLVs, the env glycoprotein is restricted to binding to avian cell receptors. Thus, these viruses cannot infect mammalian cells efficiently.

One method that has been used to overcome this limitation is to make transgenic mice that express the cellular receptor of subgroup A avian leukosis sarcoma viruses. (Federspiel et al., (1994) *PNAS* (U.S.A.) 91:11241–11245). RSV-derived vectors are able to transfer and stably express alkaline phosphatase and chloramphenicol-acetyltransferase (CAT) genes in the muscle of subgroup A receptor transgenic mice. (Federspiel et al., (1994) *PNAS* (U.S.A.) 91:11241–11245). Although the transfer of genes is efficient, ASLVs do not replicate in mammalian cells (there is a defect in virion assembly) and the RSV-derived vectors are constitutively replication-defective in mammalian cells. Moreover, use of the RSV-derived vectors is limited to the small number of mammalian host cells carrying the subgroup A avian leukosis virus receptor.

Efforts to expand the host range of retroviral vectors to a number of different cell types in a variety of mammalian species have utilized the ability of retroviral capsids to assemble with or be "packaged" by the envelope glycoproteins of other viral species. Through a mechanism that is not well understood, a pseudotyped virus bearing envelope glycoprotein that is a mixture of the two viruses is generated. (Emi et al. (1991) *J. Virology* 65:1201–1207). The pseudotyped virus has the host range of the virus donating the envelope protein. (Burns et al. (1993) *PNAS* (U.S.A.) 90:8033–8037).

For example, Emi et al. (1991) *J. Virology* 65:1201–1207 and Burns et al. (1993) *PNAS* (U.S.A.) 90:8033–8037 describe the generation of pseudotyped viruses by co-infection of the same cells with MLV and the vesicular stomatitis virus (VSV) helper/packaging virus. The resulting pseudotyped viruses have the increased host cell range of VSV (i.e. they can infect hamster cells, which MLV generally cannot infect) but at a low titer).

Landau and Littman, (1992), *J. Virology,* 66:5110–5113, describe the production of replication-defective pseudotyped viruses wherein the MLV genome bears either the MLV or ecotropic or the RSV envelope glycoprotein. The packaging system is produced by transient expression of the env genes in cells infected with replication defective MLV. The resulting MLV pseudotyped viruses have expanded host ranges.

Miller et al., U.S. Pat. No. 4,861,719 (filed Apr. 25, 1986; issued Aug. 29, 1992) and Temin et al., U.S. Pat. No. 5,124,263 (filed Jan. 12, 1989; issued Jun. 23, 1992) describe packaging/helper cell lines used to alter the host range of replication defective retroviral vectors they are co-cultivated with. Both references describe, inter alia, helper/packaging cell lines derived from amphotropic MLV.

Researchers have attempted to "package" the ASLV genome in the envelope glycoprotein of a virus with a broader host range. For example, Weiss et al., (1977) *Virology* 77:808–825, describe superinfection of cells producing RSV with temperature sensitive mutants of VSV in an effort to expand the host range of the RSV-based vectors. Two types of pseudotyped viruses resulted: VSV genomes bearing RSV envelope antigens and RSV genomes bearing VSV envelope antigens. The RSV genomes bearing the VSV envelope antigens possessed the host range of the VSV virus and were capable of infecting mammalian cells, but at a lower titer than chicken cells.

Weiss and Wong, (1977) *Virology* 76:826–834 describe mixed infection of cultured avian cells by RSV and MLV. The appearance of RSV particles infectious for mammalian cells was observed. However, the MLV env protein does not appear to compete efficiently with RSV env to form pseudotyped virus. In addition, the resulting RSV pseudotyped viruses with the xenotropic and ecotropic MLV env antigens were shown to infect mammalian cells only at a very low titer (on the order of $10^2$/ml).

In each of these references the expanded host range avian pseudotyped viruses depend on the production of an envelope protein by a help virus or packaging cell. Thus, these vector systems are susceptible to recombination between the two viral genomes and the instability and potential contamination with wild-type virus recombination engenders. Consequently, they are not suitable for gene therapy.

Some researchers have attempted to expand the host cell range of avian leukosis virus-based vectors by creating recombinant vectors which express chimeric proteins with expanded host cell binding capacity. For example, Dong et al., (1992) *J. Virology* 66:7374–7382, describe a recombinant RSV-based vector expressing a chimeric influenza virus hemagglutinin (HA). Plasmids containing chimeric HA genes comprised of the coding sequence for the RSV env signal peptide fused to the hemagglutinin (HA) structural genes or a combination of HA and RSV structural genes were used to co-infect cells with plasmids carrying RSV gag-pol-sequences. Viral particles that contained HA were formed and could be used to infect mammalian cells. However, the replication-competence of the vector in avian cells was not demonstrated and the efficiency of infection of mammalian cells was low, on the order of $10^2$/ml.

Valsessia-Wittman et al., (1994) *J. Virology* 68:4609–4619, describe the replacement of the putative receptor-binding domain of the subgroup (A) RSV envelope protein gp85 (SU) with the peptide known to be the target for cellular integrin receptor. Viral particles coated with the modified envelope were shown to infect mammalian cells which are resistant to infection by subgroup (A) ASLVs. However, infectivity of this vector in mammalian cells also appeared to be quite low, on the order of 10–$10^2$/ml.

In spite of numerous attempts in the prior art to develop vectors that were simultaneously able to: 1) efficiently infect a broad range of cell types in a variety of avian and mammalian species, independent of helper or packaging virus cell lines; and 2) unable to replicate once inside the mammalian host cell, until the present invention, such a vector remained elusive.

SUMMARY OF INVENTION

The present invention, in general, provides recombinant avian sarcoma leukosis virus (ASLV)-derived retroviral vectors having an expanded host range, thereby allowing the vector to be used for gene transfer in a variety of species. In particular, the ASLV envelope gene is replaced by the env region derived from a virus capable of infecting both mammalian and avian cells. The recombinant retroviral vectors of this invention can replicate efficiently in avian cells, allowing for production of high titer stock and they are able to infect both mammalian and avian cells at a high titer. However, the ASLV-derived vectors of this invention are replication defective in mammalian cells, thereby providing retroviral vectors that are quite safe for use in gene therapy.

It is a general object of the present invention to provide recombinant retroviral vectors that are capable of carrying one or more nucleic acid sequences of interest and expressing them in a broad range of mammalian cells.

It is a further object of the present invention to provide host cells, particularly avian or mammalian cells, carrying the recombinant retroviral vectors and capable of expressing one or more nucleic acid sequences of interest.

It is also an object of the present invention to provide methods for using the recombinant retroviral vectors to transfer nucleic acid sequences of interest into a broad range of host cell types,, both in vitro and in vivo, in a variety of species, including avian and particularly mammalian species.

It is yet another object of this invention to provide a method for using the recombinant retroviral vectors to produce transgenic animals.

It is a further object of the invention to provide transgenic animals carrying the recombinant retroviral vectors in at least one cell.

It is a further object of the invention to provide methods for treating or preventing diseases involving transfer by the recombinant retroviral vectors of all or part of a nucleic acid sequence of interest to a mammal, preferably a human.

DESCRIPTION OF THE FIGURES

FIG. 1A: A schematic depiction of the construction of plasmid RSVgagpol.

FIG. 1B: A schematic depiction of the construction of recombinant retroviral vector RCAS-M(4070A).

FIG. 2A: The structure of plasmids RSVgagpol and MLVenv shown schematically. RSVgagpol contains the gag-pol open reading frame derived from the retroviral vector RCASBP(A) Petropoulos and Hughes, (1991) *J. Virology* 65:3728–3737. MLVenv carries a region encoding the signal peptide, surface glycoprotein gp70 and transmembrane protein p15E of an amphotropic MLV, clone 4070A (Ott et al., (1990) *J. Virology* 64:757–766, Ott et al., (1992) *J. Virology* 66:4632–4638).

FIG. 2B: Immunoblotting analysis of the viral particles harvested from the complementation assay with RSVgagpol and MLVenv. Antibodies against RSV p19 (MA) and MLV gp70 (SV) were used. Lanes 1 and 2 show MLVenv recovered from supernatants of cells transfected with MLVenv plasmid alone. Lanes 3 and 4 show RSVgagpol recovered from supernatants of cells transfected with RSVgagpol plasmid alone and Lanes 5 and 6 show virus particles recovered from supernatants of cells co-transfected with both plasmids.

FIG. 3A: Schematic depictions of the structures of retroviral vectors RCAS-M(4070A) and RCASBP(A). RCAS-M (4070A) contains a chimeric env gene derived from an amphotropic MLV in place of the env gene of RCASBP(A). Retroviral vector RCAS BP(A) was modified to create RCAS-M(4070A) by replacing the env gene stop codon with a unique NotI cleavage site. Additionally, RSV env coding sequences were removed and the chimeric envelope coding region, including a new stop codon, was inserted generating the recombinant retroviral vector RCAS-M(4070A).

FIG. 3B: SDS-PAGE gel. Lanes 1 and 2 contain viral particles recovered from the transfection of CEFs with RCAS-M(4070A). Lanes 3 and 4 are controls and contain the viral particles recovered from CEFs infected with pR4070A, the molecular clone of the amphotropic MLV from which the MLV env gene was derived.

FIG. 4A: Stained cells expressing gp70 from RCAS-M (4070A). To measure the ability of RCAS-M(4070A) to replicate in CEFs, cells were transfected with RCAS-M (4070A) DNA and passaged six times to allow the virus to spread. At passages 1, 4 and 6 a small number of cells were plated separately. Those containing virus were identified by staining with antibodies that react with gp70. Only a small number of positively stained cells are seen in passage 1. This number increases significantly by passage 4. At passage 6 virtually all cells are infected and expressing gp70.

FIG. 4B: Immunoblot analysis of the viral particles recovered from the harvested CEFs cell medium at each passage with antibodies against p19 and gp70. The amount of viral proteins in the supernatant increases by passage 4 and reaches a high level by passage 6.

FIG. 5: Puromycin-resistant colonies of D17 (dog) cells produced by infecting D17 cells with serial dilutions of RCAS-M(4070A)Puro.

FIG. 6A: Schematic Structure of RCAS-M(4070A)NEO. Restriction endonuclease sites are indicated. "E" refers to EcoRI, "B" refers to BamHI.

FIG. 6B: Detection of RCAS-M(4070A)NEO provirus in the genomic DNA of infected NIH 3T3 cells by Southern blot hybridization. Lanes 1–19 show fragments derived by cleavage of the DNA of G418$^r$ clones by EcoRI and BamHI. Lane C shows fragments derived by cleavage of plasmid RCAS-M(4070A) DNA by EcoRI and BamHI.

FIG. 6C: Detection of RCAS-M(0470A)NEO provirus in the genomic DNA of infected HeLa cells by Southern blot hybridization. Lanes 1–15 show fragments derived by cleavage of the DNA of G418$^r$ clones by EcoRI and BamHI. Lane C shows fragments derived by cleavage of plasmid RCAS-M(4070A) DNA by EcoRI and BamHI.

FIG. 7: Immunoblot analysis of viral particles recovered from the culture of cells infected with RCAS-M(4070A). Antibodies against p15E were used. Lane 1 shows wild type MLV p15E proteins Lane 2 shows p15E proteins from a strain of MLV with a defective protease gene. Lane 3 shows RCAS-M(4070A) p15E proteins.

FIG. 8: A schematic depiction of mutations in the amphotropic env gene of RCAS-M(4070A)NEO. CEFs were infected with RCAS-M(4070A)NEO after 3 passages of the virus. Full-length clones of the viral DNA were derived from the library of a low-molecular-weight DNA which was extracted from infected CEFs. Env genes of clones env 1, 3, 6, 8 and 9 were sequenced and are depicted.

FIG. 9A: Replication of RCAS-M2(4070A)Puro and RCAS-M2(4070A)Puro 1, 6, 8, and 9 in CEFs as measured by a RT assay. CEFs were transfected with plasmid DNA and passaged. 24 h after transfection and at each passage, virus particles were recovered from the culture fluid by centrifugation and quantified by determination of the RT activity. The control, uninfected cells, is designated a "mock." RCAS-M2(4070A)Puro is designated "env (wt)" and RCAS-M2(4070A)Puro 1, 6, 8 and 9 are designated "env 1", "env 6", "env 8", and "env 9", respectively.

FIG. 9B: Titers of RCAS-M2(4070A)Puro1, 6, 8 and 9 on D17 cells. Cells were infected with the serial 10-fold dilutions of virus-containing culture fluid harvested at each passage. Resistant clones were selected in the medium containing puromycin. pac$^r$ colonies were stained with Giemsa stain and counted. RCAS-M2(4070A)Puro 1, 6, 8 and 9 are designated "env 1", "env 6", "env 8", and "env 9", respectively. "Cfu" means colony-forming units.

FIG. 9C: Titers of RCAS-M2(4070A)Puro8 (designated "RCAS-M2(4070A)Puro") and RCAS-M2C(4070A)Puro on D17 cells. Values shown are the average of two independent determinations.

DETAILED DESCRIPTION OF THE INVENTION

Figure 1B:
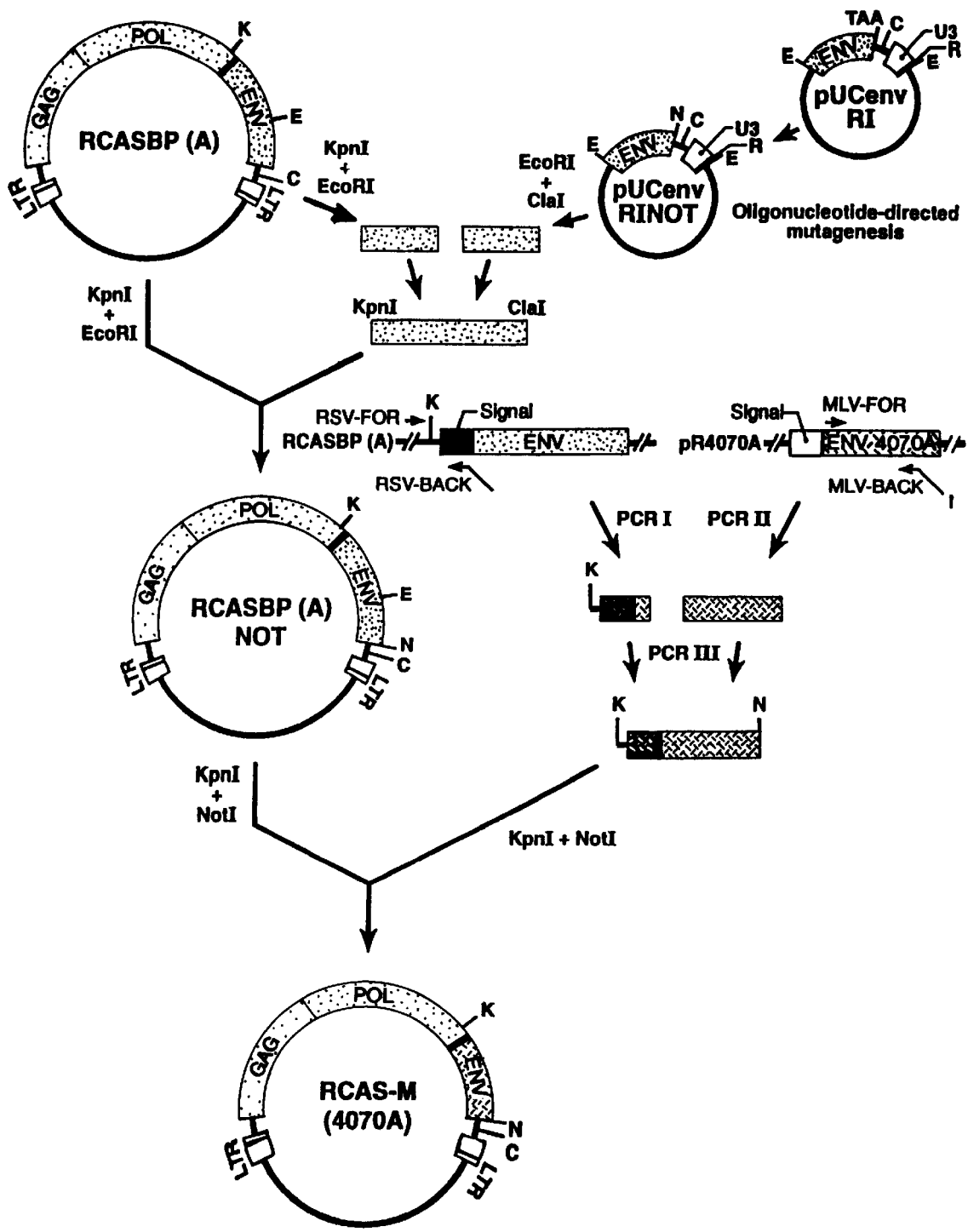

This invention relates to recombinant retroviral vectors capable of infecting a broad range of host cells, in particular both mammalian and avian cells, in high titer. In general, the recombinant retroviral vectors of this invention comprise at least one long terminal repeat (LTR), a gag region, a pol region, and an env region, or functional equivalents thereof. More specifically, the recombinant retroviral vectors comprise LTR, pol and gag regions derived from avian sarcoma leukosis viruses (ASLV) and an env region derived from a virus capable of infecting both avian and mammalian cells, such as amphotropic MLV. The recombinant vectors are capable of carrying and expressing one or more nucleic acid sequences of interest, replicate efficiently in avian cells and are able to efficiently infect and transfer genes into a broad range of mammalian cells. The recombinant retroviral vectors of the invention are replication-defective in mammalian cells, greatly enhancing their safety.

Gag is the retroviral gene which encodes the structural proteins that form the virion core. The gag region of the vector may be derived from the gag region of any member of the ASLV family. Examples of the genomes from which the gag sequence may be derived include, but are not limited to, Rous sarcoma virus (RSV), MC29-associated virus (MAV), Rous associated virus (RAV), RAV-O, avian erythroblastosis virus (AEV), avian myoblastosis virus (AMV), other members of this virus family and their associated helper viruses. The gag region may comprise all or parts of the gag gene. For a replication competent vector, it is preferable that a sequence sufficient to encode a functional gag protein is used. In a preferred embodiment the gag region is derived from RSV.

Pol is the retroviral gene which encodes the reverse transcriptase and integrase. The pol region may be derived from the pol region of any member of the ASLV family. Examples of the genomes from which the pol sequences may be derived, include, but are not limited to, RSV, MAV, RAV, RAV-O, AEV, AMV, other members of this virus family and their associated helper viruses. The pol region may comprise all or parts of the pol gene. For a replication competent vector it is preferable that a sequence sufficient to encode a functional pol protein is used. By way of example, a pol region derived from the Bryan high titer RSV strain may be used. (Petropoulos and Hughes (1991) *J. Virology*, 65:3728–3737).

Env is the retroviral gene which encodes the envelope antigens that determine the antigenic and subgroup specificity of the virus. The env sequence is preferably derived from the envelope region of a virus capable of infecting both mammalian and avian cells. Examples of the genomes from which the env sequences may be derived include, but are not limited to, mammalian viruses capable of infecting avian species, such as the amphotropic Moloney murine leukemia virus (MLV) env sequence. Weiss et al., (1982) *RNA Tumor Viruses*; Weiss (1985) Supplement to *RNA Tumor Viruses*. The env sequence may comprise all or parts of the env gene. For a replication competent virus, it is preferable that a sequence sufficient to encode a functional envelope protein is used. By way of example, a sequence encoding the complete amphotropic MLV env region may be used in the recombinant retroviral vector of this invention.

In a preferred embodiment, the coding sequence of a virus capable of infecting both mammalian and avian cells such as amphotropic MLV, is "adapted" to permit initial replication rates similar to those observed in wild type RSV via one or more mutations of the DNA of the env coding sequence, including, but not limited to, the substitution of the proline at position 242 with isoleucine. As described more fully in the examples, the "adapted" env sequence may be produced by passaging the virus and selecting for fast replicating clones. Additionally, one skilled in the art will recognize that the env sequence may be "adapted" by a number of other methods including, but not limited to, use of site directed mutagenesis to produce the desired mutation(s).

Alternatively, a chimeric envelope sequence may be used in constructing the recombinant retroviral vector of this invention, comprising the coding region of a wild type or "adapted" env gene sequence of a virus capable of infecting mammalian and avian cells and the N terminal signal peptide sequence of an ASLV.

Long terminal repeats (LTRs) facilitate integration of the viral genome into the host genome and contain promoters for transcription of the viral genome. The retroviral vectors of this invention have at least one, preferably two LTR's. A LTR derived from an ASLV family member may be used. These include, but are not limited to, RSV, MAV, RAV, RAV-O, AEV, AMV and other members of this family, and their associated helper virus. (Hughes and Kosik, (1984) Virology 136:89–99, Hughes et al., (1987) J. Virology 61:3005–3102). For a replication competent virus, preferably the entire LTR is used. Alternatively, in another embodiment, a retroviral vector with a single LTR may be used. If a single LTR circular plasmid is used, a two LTR proviral form can be simply derived by cleavage at an appropriate restriction site and ligation. (Hughes and Kosik, (1984) Virology 136:89–99).

The RSV-derived vector designated RCAS may be used to generate the recombinant retroviral vector of this invention by providing the LTR, pol and gag sequences. (Hughes et al., J. Virology (1987) 61:3004–3012; Hughes and Kosik (1984) Virology 136:99–99, herein incorporated by reference). Additionally, in another embodiment the RCASBP vectors are used. (Petropoulos and Hughes, (1991) J. Virology 65:3728–3737). In the construction of RCAS, the genome of a circular DNA form of the Schmidt Rappin A (SR-A) strain of RSV, was recloned in proviral DNA form with the E coli replicon between the LTRs of the provirus. The v-src coding region was removed and was replaced with the cleavage site for the restriction endonuclease Cla I. One copy of the direct repeats flanking v-src in SR-A was removed. To construct RCASBP, the RCAS vector was used and the pol gene of the SR-A strain was replaced by the pol gene of the Bryan high titer strain of RSV.

Figure 3A:
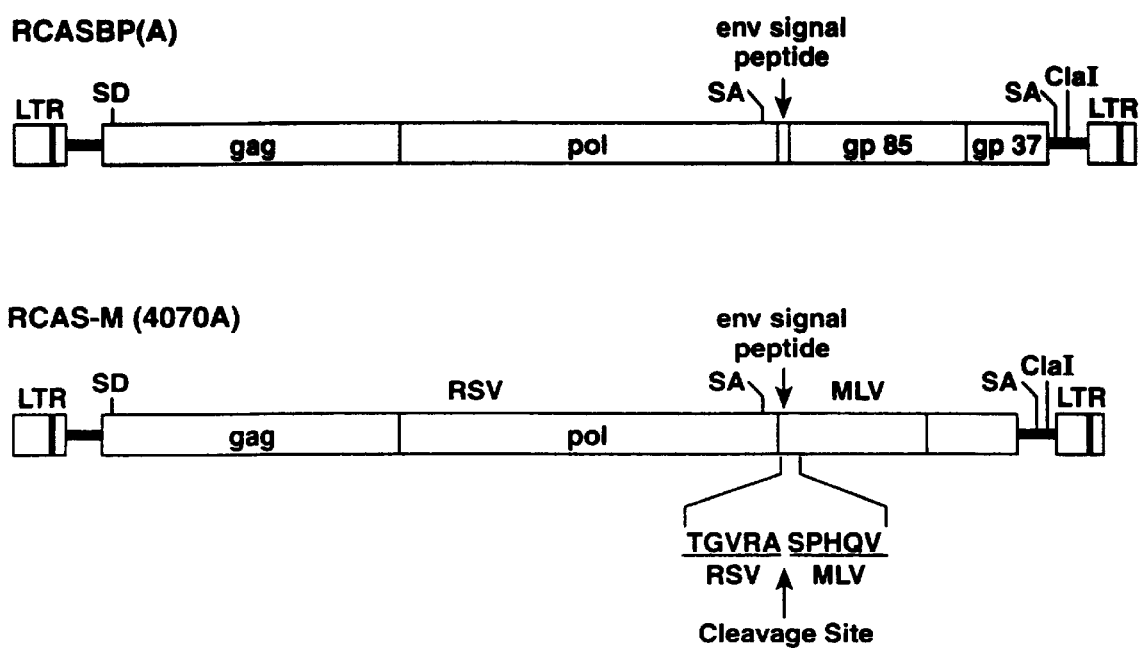

Conventional methodology may be used to replace the RSV-derived env sequence present in the RCAS or RCASBP vector with the env sequence of the amphotropic MLV retrovirus (see Example 2). The complete MLV env coding sequence may be used or a chimeric env sequence comprising the MLV env coding sequence having the RSV signal peptide in place of the MLV signal peptide may be constructed and cloned into the vector. The resulting retrovirus, designated RCAS-M (4070A), is shown in FIG. 3. The functional equivalents of the recombinant retrovirus shown in FIG. 3 are also intended to be encompassed by this invention.

In a preferred embodiment, the of RCAS-M (4070A) is "adapted" for fast initial replication by introduction of one or more mutations into the env sequence, including substitution of the proline at position 242 with an isoleucine. The resulting retrovirus is designated RCAS-M2(4070A). The functional equivalents of the RCAS-M2 (4070A) recombinant retrovirus are also intended to be encompassed by this invention.

In yet another embodiment of this invention, the envelope region of the recombinant retroviral vectors of the invention is derived from a virus that recognizes mammalian, but not avian cell receptors. In order for a vector containing such an envelope sequence to infect avian host cells, the avian cells may be engineered to express a receptor recognized by the chosen envelope region.

The recombinant retroviral vectors of this invention may be used for expression of nucleic acid sequences of interest. In this embodiment, the vector further comprises one or more nucleic acid sequences encoding a protein of interest. One skilled in the art will recognize that virtually any nucleotide sequence from virtually any genome may be used. In particular, nucleic acid sequences encoding a therapeutic or immunogenic protein may be used. Alternatively, nucleic acid sequences encoding the antisense strand for one or more proteins may be used to inhibit the expression of the proteins. The nucleic acid sequences may be inserted into the retroviral vector of this invention using conventional methodology known to those skilled in the art. Examples include, but are not limited to, cleavage by a specific restriction endonuclease and ligation or homologous recombination.

Conventional methodology including, but not limited to site directed mutagenesis, may be used to introduce one or more restriction endonuclease sites into the vectors of this invention. (Sambrook et al (eds) (1989) "Molecular Cloning, A Laboratory Manual, Cold Spring Harbor Press, Plainview, N.Y. and Ausubel et al. (eds) (1987) in "Current Protocols in Molecular Biology" John Wiley and Sons, New York, N.Y.). To retain the ability of the vectors to replicate in avian cells it is important not to delete any of the gag, pol, or env sequences necessary for virus replication. Any restriction endonuclease site may be generated, preferably an endonuclease unique to the retroviral expression vector or an endonuclease site that does not appear frequently in the vector. One of skill in the art will know how to select and create the appropriate restriction endonuclease sites.

In one embodiment, RSV is used to generate the recombinant retroviral vectors of the invention and the nucleic acid sequences of interest may be inserted in place of the RSV v-src oncogene using restriction endonucleases and ligation. In a preferred embodiment, the nucleic acid sequences of interest are inserted into the Cla I site of the RSV-derived RCAS or RCASBP vectors and at least one copy of the direct repeats flanking the v-src site are removed to increase the stability of the vector (see Example 2).

The desired nucleic acid sequences inserted into the recombinant expression vector of this invention may be transcribed under the direction of the LTR promoter. By way of example, the RSV-derived RCAS or RCASBP vectors may be used to generate the recombinant retroviral vectors of the invention when the LTR will direct the expression of the nucleic acid sequence of interest. (Hughes and Kosik, (1984) Virology 136:89–99, Hughes et al., (1987) J. Virology 61:3004–3012).

Alternatively, the expression of the desired nucleic acid sequences may be under the direction of an internal promoter within the recombinant retroviral vector of this invention. By way of example, tissue specific promoters such as a sk actin (Petropoulos and Hughes (1991) J. Virology 65:3728–3737), inducible promoters such as metallothionien (Petropoulos and Hughes (1991) J. Virology 65:3728–3737), a cell cycle or stage specific promoters may be used to direct expression of the desired nucleic acid sequences. One of skill in the art will know what promoter should be used based on the intended application of the gene product. By way of example, the RSV-derived RCAN vectors, (Hughes and Kosik, (1984) Virology 136:89–99; Hughes et al. (1987) J. Virology 6:3004–3012) may be used to generate the recombinant retroviral vectors of the invention when an internal promoter will be used. Conventional methodology may be used to incorporate these promoters into the recombinant retroviral vectors.

Additionally, one skilled in the art will recognize that a splice acceptor or an IRES (internal ribosome entry site) may be introduced in the retroviral vector to permit expression of an inserted gene.

The recombinant vectors of this invention may further include additional expression control elements, including, but not limited to enhancer sequences. Conventional methodology can be used to incorporate these additional expression control elements into the vector. (Sambrook et al (eds (1989) "Molecular Cloning, A Laboratory Manual, Cold Spring Harbor Press, Plainview, N.Y. and in Ausubel et al. (eds) (1987) in "Current Protocols in Molecular Biology" John Wiley and Sons, New York, N.Y.).

Another aspect of the present invention is to provide a method for using the recombinant retroviral vectors to transfer one or more nucleic acid sequences of interest to a broad range of host cells from a variety of species, particularly mammalian species. The recombinant retroviral vectors of the present invention may carry one or more nucleic acid sequences of interest. The virions encapsulating the nucleic acid sequences of the invention are capable of infecting a broad range of mammalian cell types. Once inside the cell, the recombinant retroviral vectors make a DNA copy of the retroviral genome and the nucleic acid sequences of interest, which is stably inserted into the host genome and can be expressed by the host cell.

The recombinant retroviral vectors of the invention may be directly introduced into a host cell or may be inserted into a plasmid or other construct which is then inserted into a host cell. For example, to generate large quantities of the retroviral vector DNA of this invention, the recombinant retroviral vectors of the invention may be cloned into a plasmid for propagation of the DNA in appropriate cells. Examples of the cells that may be used include but are not limited to *E. coli*. Construction of the plasmid containing the retroviral vector DNA can be performed by conventional methods.

By way of example the pBR322 plasmid or a derivative thereof may be used to propagate the vector DNA. In a preferred embodiment the retroviral vector of the invention is inserted into the *E. coli* replicon pPH, derived from pBR322. (Hughes et al. (1987) *J. Virology* 61:3004–3012).

It will be understood by one skilled in the art that the plasmid carrying the recombinant retroviral DNA should contain additional elements necessary for transfer and subsequent replication of the construct in the host system being used to propagate the DNA. Examples of such elements include but are not limited to origins of replication and selectively. It will be understood by one skilled in the art that the correct combination required or preferred elements to be used.

The means by which the recombinant retroviral vectors may be introduced into the host cell include, but are not limited to, microinjection, electroporation, transduction or transfection using DEAE-dextran, lipofection, calcium phosphate or other procedures known to one skilled in the art (Sambrook et al. (1989) in "Molecular Cloning. A Laboratory Manual," Cold Spring Harbor Press, Plainview, N.Y.).

Another aspect of this invention is to provide host cells into which the recombinant retroviral vector containing all or part of nucleic acid sequences of interest has been inserted. The host cells containing the recombinant retroviral vector of this invention include eukaryotes, such as avian species including ducks, chickens, turkeys, and quail, and mammalian species including mice, dogs, humans. Preferred host cells include, but are not limited to, CEF cells, NIH 3T3 cells, D17 cells and HeLa cells.

The retroviral vectors of this invention are replication competent in avian cells. Avian cells including but not limited to, chicken, turkeys, quail, and duck may be used to generate a viral stock. The viral stock may be generated by methods known to those skilled in the art. The recombinant retroviral vector cloned into a plasmid may be introduced into the avian cells by conventional methodology and the cells may be passaged to allow the virus to spread throughout the culture. Subsequent generations of the virus may be used to infect other cells. Alternatively, a virus carrying the recombinant retroviral vector may be used to infect the avian cells. The viral stock produced may be used to infect other host cells. Examples of cells that may be infected include but are not limited to, duck, chicken, turkeys cells or mammalian cells. Examples of mammalian cells include but is not limited to hematopoietic stem cells, islet cells, or T-cells.

Host cells containing a recombinant retroviral vector of the invention can be used in vitro to produce recombinant proteins. The recombinant proteins can be isolated and purified by conventional methods. (Sambrook et al (eds) (1989) "Molecular Cloning, A Laboratory Manual, Cold Spring Harbor Press, Plainview, N.Y. and in Ausubel et al. (eds) (1987) in "Current Protocols in Molecular Biology" John Wiley and Sons, New York, N.Y.). Additionally, host cells may be used in vivo to supply recombinant proteins.

In another embodiment, the recombinant retroviral vectors of the invention may be used to transfer nucleic acid sequences encoding one or more therapeutic proteins to a mammal, preferably a human, in need of gene therapy. The retroviral vector carrying the nucleic acid sequence of interest may be administered to an individual in need of such therapy in a variety of ways. Retroviral supernatants from avian host cells transfected with and producing the virus may be administered to the individual in need of gene therapy. Additionally, a substantially purified form of the virus may be administered to the mammal in need of such treatment alone or in the form of a pharmaceutical composition.

Alternatively, the gene therapy may be accomplished by inserting the nucleic acid sequences encoding the therapeutic protein(s) into the recombinant retrovirus vector of the invention and introducing it into a host cell. The host cell which contains the recombinant retroviral vector and expresses the desired therapeutic protein is then administered to or implanted in the individual in need of gene therapy. The cells then express the therapeutic protein recombinantly in the mammal.

The host cells may be from virtually any species. In one embodiment, the host cells are taken from the individual in need of the gene therapy. Examples of such host cells include, but are not limited to, hematopoietic stem cells or T cells. In another embodiment the host cells are not from the individual receiving the therapy, but are from different species. For example, in one embodiment, which takes advantage of the ability of the retroviral vectors of the invention to replicate and produce virus in avian but not mammalian cells, avian host cells containing the retroviral vector are administered to a mammal in need of therapy.

Means of administering the host cell containing the recombinant retroviral vectors of the invention which recombinantly express the proteins of interest include, but are not limited to, intravenous, intramuscular, intralesional, subcutaneous or intraperitoneal injection or implantation. Alternatively, the cells containing the recombinant retroviral vectors may be administered locally by topical application, direct injection into an affected area or implantation of a porous device containing cells from the host or another species in which the recombinant retroviral vectors are inserted and which express the proteins of interest.

Examples of diseases that may be suitable for gene therapy include, but are not limited to, neurodegenerative diseases or disorders, Alzheimer's, schizophrenia, epilepsy, neoplasms, cancer and AIDS.

In yet another aspect of the invention, the recombinant retroviral vectors can be used to generate transgenic animals carrying the recombinant vector in at least one cell. In a preferred embodiment, the recombinant retroviral vector carrying one or more nucleic acid sequences of interest is introduced into an animal or an ancestor of the animal at an embryonic stage. The transgenic animal can be made by several methods, including, but not limited to, introducing the recombinant retroviral vector carrying the nucleic acid sequences of interest into the embryonic animal by infection or injection. Additionally, the recombinant retroviral vector may be inserted into host cells which are then introduced into the developing embryo. By way of example, chicken cells containing the recombinant retroviral vector and carrying the gene of interest can be implanted into the blastocyst stage of a mammalian embryo.

Examples of animals into which the recombinant retroviral vector can be introduced include, but are not limited to, non-human primates, cows, sheep, dogs, mice, rats, or other rodents. Such transgenic animals may be useful as biological models for the study of disease and to evaluate diagnostic or therapeutic methods for disease.

It will be appreciated by those skilled in the art that the recombinant retroviral vectors of this invention may be used to generate transgenic animals without additional nucleic acid sequences (e.g. insertional mutagenesis). Alternatively, nucleic acid sequences of interest may be inserted into the recombinant retroviral vectors of the invention such that the transgene animal expresses the desired gene(s).

It is a further aspect of the invention to use the recombinant retroviral vectors to deliver a prophylactic or therapeutic vaccine for a wide variety of mammalian, and particularly human, diseases.

A prophylactic vaccine is provided in advance of any evidence of the disease of interest and serves to prevent or attenuate the disease in a mammal. In a preferred embodiment, mammals, preferably humans, at high risk for the disease of interest, are treated prophylactically with the vaccines of this invention.

When provided therapeutically, the vaccine is provided at or shortly after the onset of the disease of interest (or symptoms of the disease of interest) to enhance the immune response of a patient (a mammal, preferably a human) to the disease of interest and to attenuate the disease.

The vaccine, which acts as an immunogen, may be in the form of a cell transfected with the recombinant retroviral vector of the invention carrying nucleic acid sequences encoding all or part of one or more immunogenic peptides associated with the disease of interest. The vaccine may also be in the form of a culture supernatant from cells producing viral particles or a preparation of viral particles containing the retroviral vectors of interest with the inserted nucleic acid sequences of interest.

When the vaccine is used in the form of a host cell, the recombinant retroviral vector of the invention can be introduced into virtually any mammalian cell. The means by which the vector carrying the gene may be introduced into a cell include, but are not limited to, infection or other procedures known to one skilled in the art (Sambrook et al. (eds) (1989) *Molecular Cloning. A Laboratory Manual*, Cold Spring Harbor Press, Plainview, N.Y.). The mammalian cells infected with the recombinant retrovirus vectors of the invention and expressing the immunogenic protein can be administered to mammals and serve as a vaccine. Cells expressing the immunogenic protein of interest can be administered intravenously, intramuscularly, intraperitoneally, intralesionally or subcutaneously.

Additionally, the vaccine may be administered as a preparation of viral particles. Viral particles containing the recombinant retroviral vectors may be directly administered to the mammal several ways, including, but not limited to exposure of cells to virus ex vivo or injection of the retrovirus into the affected tissue or intravenously. Alternatively, viral particles carrying all or part of the nucleic acid sequences of interest may be administered locally by direct injection into an affected area or by topical application in a pharmaceutically acceptable carrier.

Examples of mammals to which the vaccine may be administered include, but are not limited to, mice, rats, dogs, non-human primates, and humans with a family history of the disease of interest. Veterinary uses are intended to be encompassed by this invention.

Vaccination can be conducted by conventional methods. The recombinant viral vectors containing the nucleic acid sequences encoding the immunogenic protein may be administered once or at periodic intervals until a significant titer of antibody or immune cells against the immunogen protein of interest is produced. One skilled in the art will know the proper immunoassays and other methods for detecting and measuring the presence of immune cells against the protein of interest.

The recombinant retroviral vector expressing the immunogen may be administered in a pure or substantially pure form. Additionally, it is possible to present it as a pharmaceutical composition, formulation or preparation.

The pharmaceutical compositions, formulations or preparations of the present invention, both for veterinary and for human use, may comprise an immunogen as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0 M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11–10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1–3.0 osmoles, preferably in the range of 0.8–1.2. The pH of the aqueous solution is adjusted to be within the range of 5.0–9.0, preferably within the range of 6–8. In formulating the immunogen of the present invention, anti-adsorption agent may be used.

After immunization, the efficacy of the vaccine can be assessed by production of antibodies or immune cells that recognize the antigen, as assessed by techniques known to those skilled in the art. If the mammal to be immunized is already afflicted with the disease of interest, the vaccine can be administered in conjunction with other therapeutic treatments.

One of skill in the art will know the parameters to determine the correct titer of particles to be administered. The quantity of recombinant retroviral vector or virus carrying all or part of the nucleic acid sequence encoding the immunogenic protein of interest to be administered may be based on the titer of virus particles. The amount of virus to be administered is in no way limited to a particular concentration and may vary depending upon the individual being healed. Based on clinical parameters the treating physician will determine the therapeutically effective amount of the virus containing the gene of interest to be administered to a given individual. Such therapy may be administered as often as necessary and for the period of time judged necessary by the treating physician. The therapeutic methods described herein may be used alone or in conjunction with additional therapy known to those skilled in the art for the treatment of a given disease or condition in a mammal.

All books, articles, or patents referenced herein are incorporated by reference. The following examples illustrate various aspects of the invention, but in no way are intended to limit the scope thereof.

EXAMPLE 1

The Amphotropic MLV Env Protein Efficiently Assembles with RSV Gag Proteins In order to investigate directly the ability of RSV gag and MLV env to assemble, a complementation assay in which gag proteins of RSV and the envelope glycoproteins of MLV were transiently expressed in chicken embryo fibroblasts (CEFs) derived from EV0 chicken embryos was developed. (Astrin et al., (1979) Nature 282:339–341. See also Hughes and Kosik (1984) Virology 136:89–99, Hughes et al., (1987) J. Virology 61:3004–3012). The CEFs used in this experiment and the other examples were maintained in Dulbecco modified Eagle medium (DMEM, GIBCO BRL, MD) supplemented with 5% fetal bovine serum, 5% newborn calf serum, 10% tryptose-phosphate broth (GIBCO BRL), 100 u/ml penicillin and 100 μg/ml streptomycin.

Construction of the Plasmids

Figure 2A:
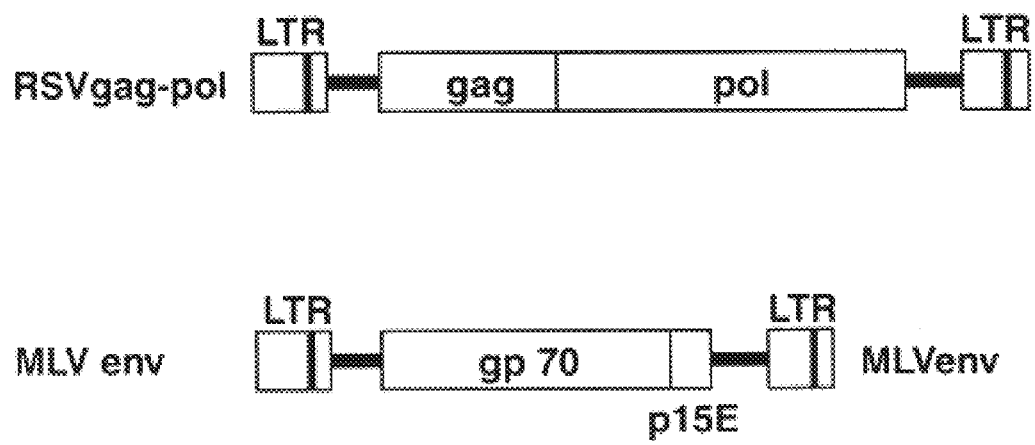

Two plasmids, RSVgagpol (which contains the gag-pol open reading frame derived from the retroviral vector RCASBP(A) (Petropoulos and Hughes, (1991) J. Virology 69:3728–3737)) and MLVenv (which carries a region encoding the signal peptide, surface glycoprotein gp70 and transmembrane protein p15E of an amphotropic MLV (clone 4070A))(FIG. 2A) were constructed by standard methods. See Sambrook et al., (eds) (1989) Molecular Cloning. A Laboratory Manual, Cold Spring Harbor Press, Plainview, N.Y. Recombinant clones were isolated in E. coli DH5a.

Plasmid RSVgagpol was constructed as follows: plasmid DNA RCASBP(A) (Petropoulos and Hughes, (1991) J. Virology 69:3728–3737 was cleaved by restriction endonucleases Sac I and Xba I (FIG. 1A) and the fragment containing the complete gag region and the 3'-end of pol was isolated. In a separate reaction, RCASBP(A) was digested by Xho I. The Xho I ends were filled in using T4 DNA polymerase and the DNA was subsequently digested by Xba I. The fragment Xba I-Xho I(blunt) containing the 3'-end of the pol open reading frame was isolated. The Sac I-Xba I and Xba I-Xho I (blunt) fragments were ligated in the presence of pBluescript KS II DNA that had been cleaved by Sac I and Eco RV. The resulting plasmid pT7gagpol contained the whole gag-pol region flanked by unique Sac I and Cla I sites. RCASBP(A) was digested by Sac I and Cla I to remove gag-pol-env region, and Sac I-ClaI fragment from pT7gagpol was inserted.

To construct plasmid MLVenv, the env coding region of the amphotropic MLV was PCR-amplified from a plasmid pR4070A (Ott et al., (1990) J. Virology 64:757–766, Ott et al., (1992) J. Virology 66:4632–4638) (kindly provided by Alan Rein, ABL-Basic Research Program) with the forward primer AMPH-F (AAAAGAGCTCGGCCGACACCCAGAGTGGAC) (SEQ ID NO: 1) located just upstream env initiation codon and the reverse primer AMPH-R (AAAAGAGCTCTCATGGCTCGTACTCTATGGGTT) (SEQ ID NO:2)spanning the env termination codon. The resulting Sac I recognition sites were included in the 5'-ends of both primers. PCR product was cleaved by Sac I and inserted into the vector TFA-NEO (Federspiel et al., (1989) J. Virology 173:167–177), generating MLVenv. This construct expresses amphotropic env gene under the transcriptional control of the RSV LTR.

Transfection of Cells and Preparation of Virus Particles

Plasmids RSVgagpol and MLVenv were introduced into CEFs by transfection both separately and in the mixture. Calcium phosphate-mediated transfection of plasmid DNAs into CEFs was performed according to standard procedures Graham and Van der Eb, (1973) J. Virology 52:456–467. Precipitates containing 10 μg of DNA per 10 mm-plate were incubated with subconfluent CEF monolayers for 6 hr at 37° C. followed by the incubation with the medium containing 15% glycerol for 5 min at 37° C. Cells were washed twice with the phosphate-buffered saline (PBS) and incubated in a growth medium for 24 hr. When necessary, transfected cells were passaged to allow the virus to spread through the culture.

Virus-containing culture fluid was then harvested. 24 hr after transfection, the culture medium was harvested and viral particles were recovered by ultracentrifugation. To prepare virus particles, culture fluid was clarified by low-speed centrifugation and the virus was pelleted through 15% sucrose cushion in SW41 rotor (Beckman) at 35,000 rpm for 1 hr at +4° C. The resulting pellet was resuspended in protein sample buffer and heated at 100° C. for 4 min before loading on a gel.

Immunoblot Analysis

Viral proteins were resolved by electrophoresis in a 4–20% gradient sodium dodecyl sulfate-polyacrylamide gel (SDS-PAGE). After electrophoresis proteins were electroblotted onto a nitrocellulose membrane (BA85, Schleicher & Schuell, NH). RSV matrix protein was detected by incubation with rabbit antiserum against p19 (MA) (generously provided by Volker Vogt, Cornell University). MLV envelope glycoproteins were detected with goat antiserum against gp70 (SU). Protein bands were visualized using enhanced chemiluminescence (ECL) detection system (Amersham).

Figure 2B:
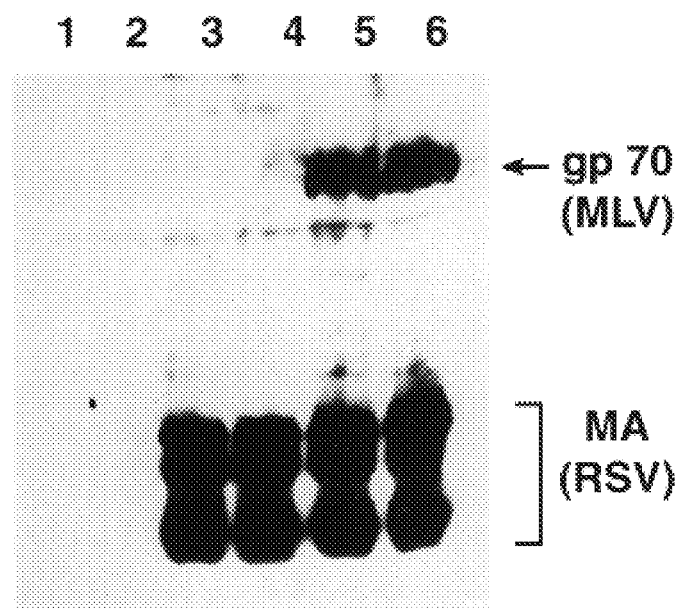

The immunoblotting analysis (FIG. 2B) showed that MLVenv plasmid, when introduced into CEFs, expresses surface glycoproteins that are anchored on a cell membrane and can be detected by immunoblotting in a membrane protein fraction (data not shown) but are not secreted into the medium (FIG. 2B, lanes 1 and 2). Transfection of RSVgag-pol results in a synthesis of capsid proteins that assemble into virus-like particles that can be recovered by ultracentrifugation (FIG. 2B, lanes 3 and 4). More than one band was detected by the anti-p19 antibodies. Since RSV MA is phosphorylated in several positions, additional bands usually seen on immunoblots apparently represent proteins with different degree of phosphorylation. Burstein et al., (1992) *J. Virology* 66:1781–1785.

Co-transfection of RSVgagpol and MLVenv causes the co-expression of both capsid and envelope proteins in the same cell. Immunoblotting analysis shows that both the RSV gag and MLV env are present in the particles produced upon co-transfection (FIG. 2B, lanes 5 and 6) suggesting that pseudotyped virions are formed.

This data shows that the amphotropic MLV envelope can associate efficiently with an RSV virion if competing RSV envelope is not present.

EXAMPLE 2

The Recombinant Retroviral Vector RCAS-M (4070A) Construction of RCAS-M(4070A)

Given the apparent efficiency with which the MLV envelope protein assembles with RSV gag, recombinant RSV genome was constructed in which the envelope gene in the parental virus was replaced with the env gene of an amphotropic MLV. To ensure the efficient intracellular transport of the envelope precursor and the signal peptide cleavage in avian cells, a chimeric env gene in which a sequence encoding a mature MLV gp70 was fused to the RSV envelope signal peptide. RSV env coding sequences were removed and the chimeric envelope coding region, including a new stop codon was inserted, generating the recombinant retroviral vector RCAS-M(4070A).

The recombinant retroviral vector RCAS-M(4070A) was prepared as follows. First, an Eco RI fragment of RCASBP (A) spanning the 3'-end of the RSV env gene and U3R segment of the 3'-LTR was subcloned in pUC19, giving rise to pUCenvRI (FIG. 1B). The termination codon for env was replaced by a Not I site using site-directed mutagenesis. Clones containing mutant plasmids with the Not I site were propagated in *Escherichia coli* BMH 71-18 mutS (Clontech) and selected by Not I cleavage. The resulting construct was called pUCenvRINOT (FIG. 1B).

The env gene of RCASBP(A) was replaced with the one carrying Not I site. RCASBP(A) was digested by Kpn I and Cla I and the fragment containing env region was removed. The env region containing the unique Not I site was introduced by ligating a Kpn I-Eco RI fragment of RCASBP(A) and the Eco RI-Cla I fragment from pUCenvRINOT with RCASBP(A) that had been cleaved by Kpn I and Cla I, generating plasmid RCASBP(A)NOT (FIG. 1B).

Overlap extension, Horton et al., (1990) *Biotechniques* 8:528–535, was used to construct a chimeric amphotropic env gene in which the sequence coding for the N-terminal signal peptide of MLV was replaced with the equivalent sequence from the RSV env gene. A fragment spanning the unique Kpn I site, the env splice acceptor site and the signal peptide was amplified from RCASBP(A) by PCR using primers RSV-FOR (GGACGAGGTTATGCCGCTGTG) (SEQ ID NO: 3) and RSV-BACK (ACATTAAAGACCTGATGGGGGCTAACATCAGCT CTTACCCCCGTAA) (SEQ ID NO: 4) (FIG. 1B). The fragment beginning with the codon for the first serine residue of the mature gp70 and spanning the whole env open reading frame followed by the unique Not I site was amplified from pR4070A with the primers MLV-FOR (AGCCCCCATCAGGTCTTTAATGT) (SEQ ID NO: 5) and MLV-BACK (AGCGGCCGCTCATGGCTCGTACTCTATGGGTT) (SEQ ID NO: 6) (primer MLV-FOR overlapped RSV-BACK). These two fragments were fused and a product amplified by PCR with the primers RSV-FOR and MLV-BACK. The resulting PCR product which contained a chimeric env gene was cleaved by Kpn I and Not I. The env gene was removed from RCASBP(A)NOT by digesting with Kpn I and Not I, and a chimeric Kpn I-Not I fragment was inserted, generating a final plasmid RCAS-M(4070A). The correct sequence of the region containing the junction between RSV and MLV env sequences was confirmed by sequencing using Sequenase Sequencing Kit (USB, OH). The structure of RCAS-M(4070A) is shown schematically on FIG. 3A.

Production of Recombinant Viral Particles by RCAS-M(4070A)

Figure 3B:
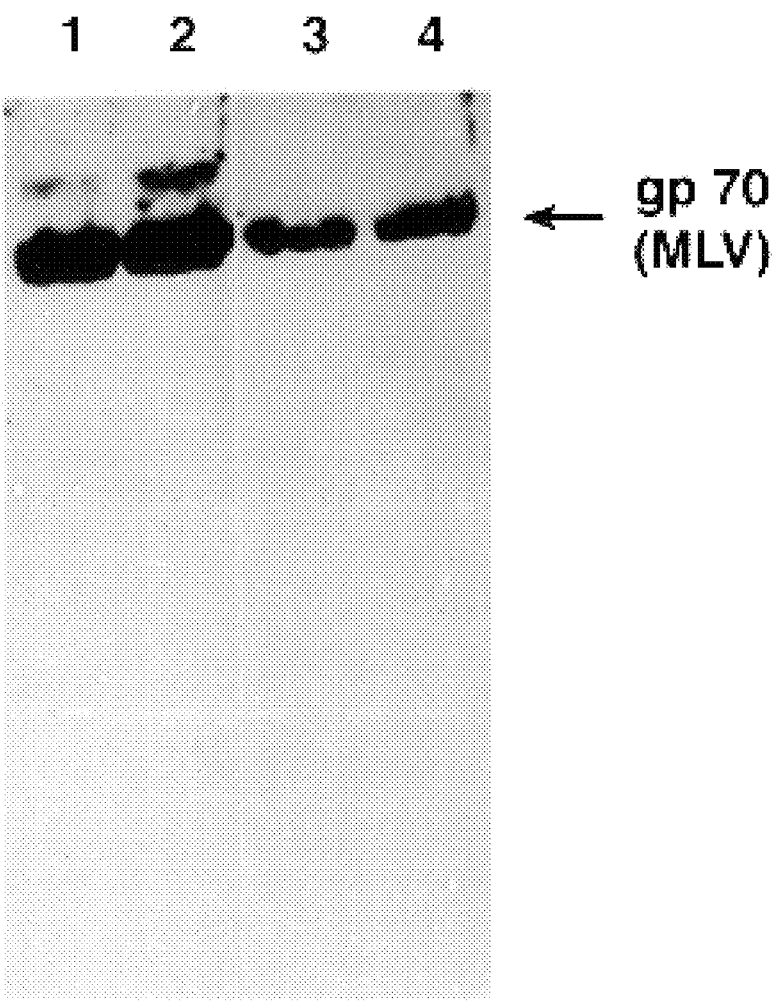

To test the expression of a chimeric env gene in a context of an RSV genome and the ability of the vector to produce particles that had incorporated the MLV surface glycoproteins, CEFs were transfected with the RCAS-M (4070A) DNA, as described in Example 1. CEFs transfected with the pR4070A, the molecular clone of the amphotropic MLV from which the MLV env gene was derived served as a positive control. 24 hr after transfection, cell culture medium was harvested and viral particles recovered by ultracentrifugation as described in Example 1. As can be seen in FIG. 3B, CEFs transfected with RCAS-M(4070A) generate particles that contain the MLV surface glycoprotein (lanes 1 and 2). Lanes 3 and 4 of FIG. 3B contain the control viral particles from the cells transfected with the amphoteric MLV. The incorporation of gp70 into a particles produced by RCAS-M(4070A) appeared to be approximately as efficient as the incorporation into MLV virions (compare lanes 1 and 2 with lanes 3 and 4).

Replication of RCAS-M(4070A) in CEFs

Having demonstrated that the recombinant retroviral vector RCAS-M(4070A) produced chimeric viral particles, its ability to replicate in CEFs was measured. CEF cells were transfected with RCAS-M(4070A) DNA as described in Example 1 and passaged to allow the virus to spread. A total of six passages were done. At passages 1, 4 and 6, a small number of cells was plated separately, and the ability of the virus to spread was measured by the staining of CEFs by the antibodies that react with expressed gp70.

The indirect immunofluorescence microscopy assay was performed as follows. CEFs infected with RCAS-M(4070A) were grown on glass slides. Cells were fixed with methanol, reacted with anti-gp70 goat serum (diluted 1:200 in PBS-1% bovine serum albumin), washed 3 times for 5 min with PBS containing 0.1% Triton X-100 and incubated with fluorescein isothiocyanate (FITC)-conjugated rabbit anti-goat secondary antibody. Photomicroscopy was performed by using a Nikon Microphot-FXA microscope (Nicon Inc., Melville, N.Y.). As shown in FIG. 4A, only a small number of positively stained cells are seen initially (passage 1). This number increases significantly by passage 4 and at passage 6 virtually all cells are infected and expressing gp70.

To monitor the production of virus particles, cell culture medium at each passage was harvested and particles were recovered by ultracentrifugation as described in Example 1. The viral particles were analyzed by immunoblotting with the antibodies against p19 and gp70 as described in Example 1. The amount of viral proteins in the supernatant increases by passage 4 and reaches a high level by passage 6 (see FIG. 4B). The ability of RCAS-M(4070A) to spread in the CEF culture is comparable to the rates of spreading seen with the parental vector RCASBP(A).

The data show that the chimeric retrovirus replicates in the avian cells at rates comparable to the original RSV-based retroviral vector. The particles of RCAS-M(4070A) generated after transfection into CEFs contain approximately the same amount of the gp70 as do particles of the amphotropic MLV, and can infect mammalian cells. Taken together, these data suggest that the initial association of the RSV gag and the amphotropic MLV env proteins is efficient enough to allow the assembly of the infectious virions.

TABLE 1

Titer of RCAS-M(4070A)Puro on mammalian cells.

| Species | Cell line | Titer |
|---------|-----------|-------|
| Mouse   | NIH 3T3   | $7.1 \times 10^4$ |
| Dog     | D17       | $5-7 \times 10^5$ |
| Human   | HeLa      | $3.3 \times 10^4$ |

Gene Transfer to Mammalian Cells by RCAS-M (4070A).

To demonstrate the ability of RCAS-M (4070A) viral particles to infect and transfer genes to mammalian cells, the marker gene pac, that confers resistance to the antibiotic puromycin (de la Luna, et al. (1988) Gene 62:121–126, Vara et al., (1986) Nucleic Acids Res. 14:4617–4624), was introduced into the Cla I cleavage site downstream of the env gene and splice acceptor to generate the vector RCAS-MC (4070A) Puro.

To facilitate cloning into RCAS-M(4070A), a silent point mutation was used to eliminate the Cla I site in the amphotropic env region. It was introduced by site-directed mutagenesis. The Kpn I-Not I-fragment of RCAS-M (4070A) was first subcloned into pBluescript KS II for mutagenesis. Mutant clones selected by Cla I cleavage were propagated in *Escherichia coli* BMH 71-18 mutS. The env region in RCAS-M(4070A) was replaced with the mutant Kpn I-Not I fragment, giving rise to a vector RCAS-MC (4070A).

To construct RCAS-MC(4070A)Puro, the puromycin resistance gene (pac) was amplified by PCR from the plasmid pSVpac (de la Luna et al., (1988) Gene 62:121–126; Vara et al., (1986) *Nucleic Acids Res.* 14:4617–4624) with the primers that appended Nco I and Hind III sites to the 5'- and 3'-ends of pac respectively. The product was then cloned into the adaptor plasmid Cla12Nco. Hughes et al., (1987) *J. Virology* 61:3004–3012. The pac gene was isolated from the adaptor construct as a Cla I-fragment and introduced into RCAS-MC(4070A).

CEFs were transfected with RCAS-MC(4070A)Puro as described in Example 1 and passaged 6 times. Virus-containing culture fluid was used to infect fresh cells that were passaged two more times. The resulting virus was titered on murine cells (NIH 3T3), human (HeLa) cells and D17, dog kidney cells. Titration on mammalian cells was performed as follows. Virus-containing culture fluid was harvested and filtered through a 0.45 μm membrane. Host cells were plated in 60-mm plates ($5 \times 10^5$ cells per plate) and grown overnight. Cells were infected with serial dilutions of the retroviral vector stocks in the presence of polybrene (10 μg/ml) for 24 h, trypsinized and plated in a selective medium containing G418 (400 μg/ml, GIBCO BRL) or puromycin (2.5 μg/ml, Sigma). Ten days later, colonies that developed from resistant cells were fixed with methanol, stained with Giemsa stain and counted. In some experiments, individual colonies were isolated and expanded into cell lines for further analysis.

Figure 5:
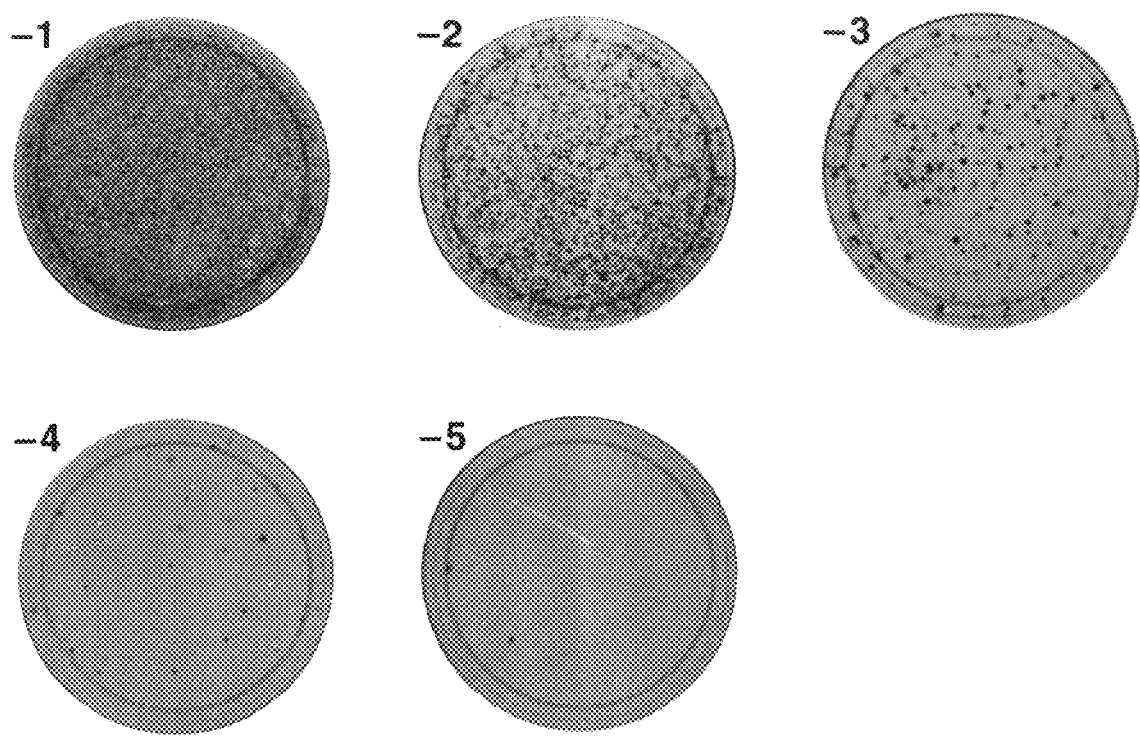

Puromycin-resistant colonies of D17 cells produced by infecting the cells with the serial dilutions of RCAS-MC (4070A)Puro are shown in FIG. 5.

Table 1 shows that RCAS-MC (4070A) Puro was able to infect each of the mammalian cells tested in high titers. The titer of RCAS-MC(4070A)Puro on D17 (dog) cells was approximately a one order of magnitude higher than the titer on NIH 3T3 (mouse) or HeLa (human) cells. The variable efficiency with which RCAS-MC(4070A)Puro infects these cells could be attributed to the differences in the amphotropic receptor density on the surface of mammalian cells of different tissues and species.

Replication and Infectivity of RCAS-M(4070A) NEO

Figure 6A:
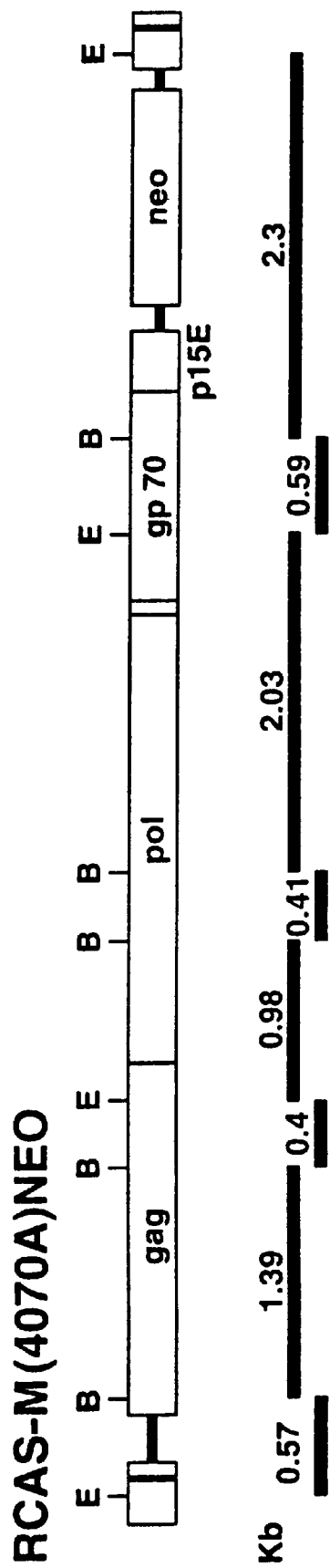

Additionally, the marker gene neo was introduced into RCAS-M(4070A). The resulting vector, RCAS-M(4070A) NEO (FIG. 6A), was used to infect and transfer genes to mammalian cells. RCAS-M(4070A)NEO was constructed as follows: The ClaI-fragment containing the neo gene was isolated from RCASBP(A)NEO and cloned into the ClaI site of RCASBP(A)NOT. The chimeric env gene was transferred into this plasmid as a KpnI-NotI fragment.

Figure 6B:
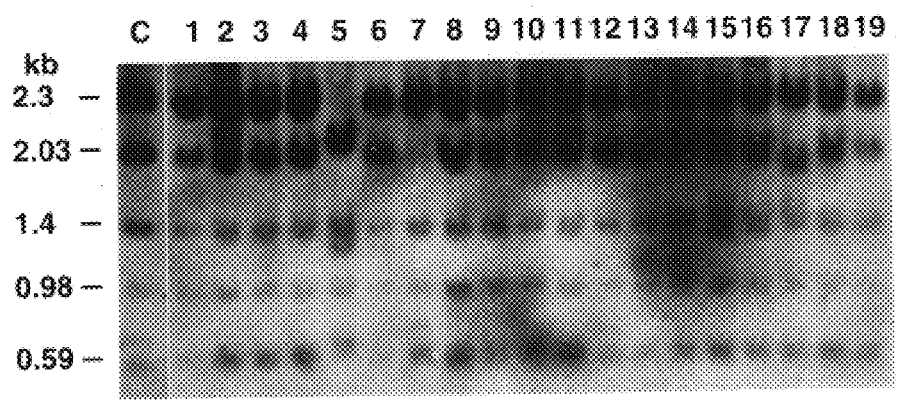
Figure 6C:
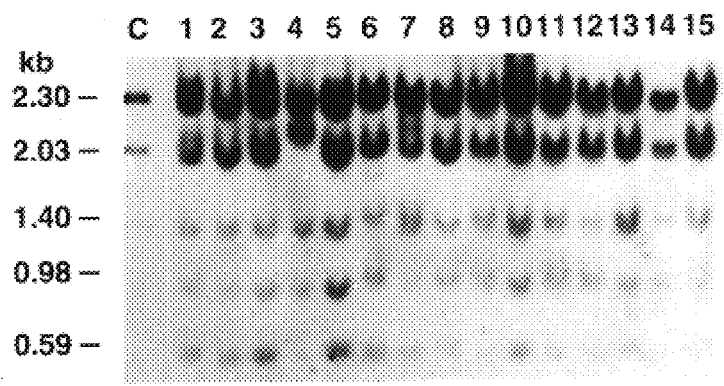

CEFs were transfected with RCAS-M(4070A)NEO as described in Example 1, and viral stocks that were generated 24 hours after transfection were titered on murine NIH 3T3 and human HeLa cells as described above. The virus obtained by the transient expression of the RCAS-M (4070A)NEO in CEFs had the titer $2-3 \times 10^3$ colony forming units (cfu/ml) on both cell lines. Genomic DNA isolated from the G418$^r$ clones was analyzed by southern blot hybridization. Cells were infected by RCAS-M(4070A) NEO and G418$^r$ clones were selected. Their genomic DNA was digested with EcoRI and BamHI. Fragments were resolved in agarose gel, transferred onto charged nylon membrane, and hybridized with digoxygenin-labeled EcoRI-digested RCAS-M(4070A)NEO DNA. Membranes were incubated with alkaline phosphatase-conjugated antidigoxygenin antibody, and bands were detected using Lumi-Phos 530 reagent. As shown in FIGS. 6B and C, the majority of the G418r clones derived from NIH 3T3 and HeLa cells contained provirus that was structurally indistinguishable from the RCAS-M(4070A)NEO.

The transfected CEFs were passaged and the produced virus was used to infect both fresh CEFs and mammalian cells. By immunoblotting analysis of the viral particles collected at each passage, it was determined that the virus replicated reasonably efficiently in CEFs; however, the ability to transfer neo$^r$ into NIH 3T3 cells decreased relatively rapidly (Table 2) and was several orders of magnitude lower than the titer of RCAS-M(4070A)Puro at a similar passage (compare Table 1 and Table 2). Sequencing of the proviral DNA as described in Example 5 showed that the neo gene was somewhat unstable in the context of the amphotropic env gene and specifically that a number of proviruses suffered deletions involving the splice acceptor site, initiation codon and 5' end of the neo gene.

It appears that the difference in stability between the neo and pac selectable markers is not a function of the vector, but rather a measure of the relative cytotoxicity of these markers on the host cell. It seems unlikely that there is a much greater tendency for the neo insert to rearrange because this would imply that there are certain preferred sites for rearrangement in the neo insert. However, the neo deletions that were analyzed were all different.

TABLE 2

Titer of RCAS-M(4070A)NEO on NIH 3T3 cells

| Virus | Titer, cfu/ml |
|---|---|
| 24 h posttransfection | $2.6 \times 10^3$ |
| Virus passage 1 | $10^1$ |
| Virus passage 2 | $10^1$ |
| Virus passage 3 | $5 \times 10^2$ |

EXAMPLE 3

Transmembrane Protein p15E is Correctly Processed in RCAS-M(4070A) Particles

In the murine leukemia viruses, the env precursor is initially cleaved by a cellular protease into gp70 (SU) and pre-p15E (TM). After the virus particle is released from the cell, the viral protease removes the C-terminal 16 residues from the cytoplasmic domain of pre-p15E, yielding the mature p15E and p2E. Rein et al., (1994) J. Virology 68:1773–1781. This cleavage activates the membrane fusion capability of the env protein and is essential for viral infectivity.

Figure 7:
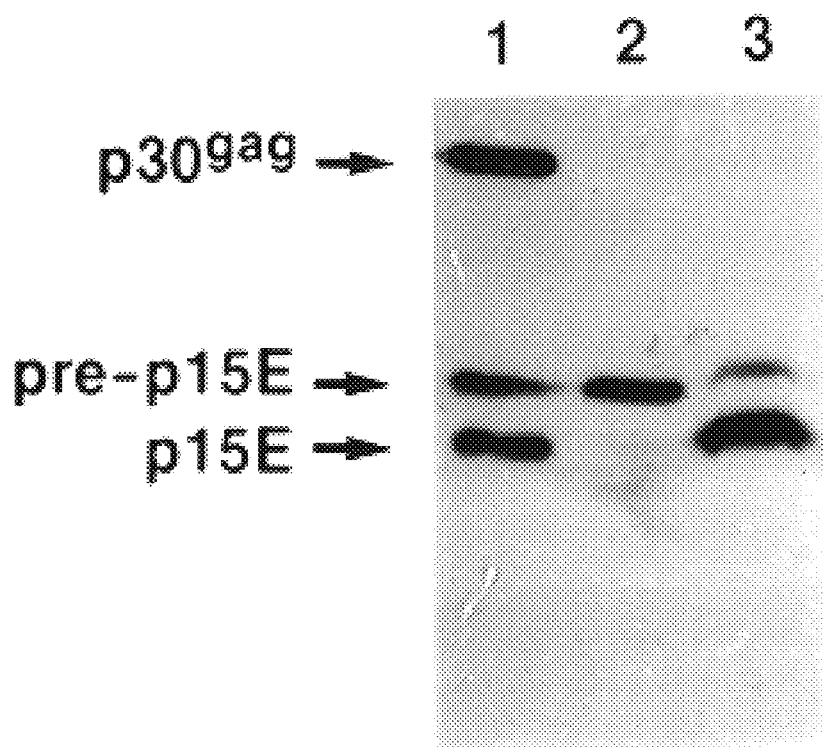

Virions produced by cells infected with RCAS-M(4070A) do not contain MLV protease. However, the chimeric virus is infectious, suggesting that pre-p15E is cleaved. Viral particles were prepared as described in Example 1 and the proteins were fractionated on 16% SDS-PAGE and analyzed by immunoblotting with rabbit antiserum against p15E (kind gift of Alan Rein) (FIG. 7). The data shows that the chimeric virus particles formed by RCAS-M(4070A) contain the processed p15E, although the MLV protease is not present. The transmembrane protein processing in the RCAS-M(4070A) particles appears to be as efficient as in the wild type MLV virions (compare lanes 1 "MLV" and 3 "RCAS-M(4070A)" of FIG. 7), suggesting that either RSV protease or the protease of the avian cells can effectively process pre-p15E.

EXAMPLE 4

Virus Particles are not Produced by Mammalian Cells Infected with RCAS-M(4070A)

Recent studies demonstrated the development of the lymphomas in the non-human primates after gene transfer as a result of infection and spreading of the replication-competent helper MLV which was present in the retroviral vector stocks. (Donahue et al., (1992) J. Exp. Med. 176:1125–1135; Vanin et al., (1994) J. Virology 68:4241–4250). This illustrates the considerable importance of the issue of a retroviral vector safety. One of the advantages of using avian retrovirus-based vectors in a mammalian cell system is that the mammalian cells transfected or infected with RSV do not produce infectious viral particles (Federspiel et al., (1994) PNAS (U.S.A.) 91:1124–11245) and therefore the vector cannot spread in the mammalian host. Inability of RSV to synthesize or to export into the cytoplasm a full-length genomic RNA, (Berberich et al., (1990) J. Virology 64:4313–4320; Knight et al., (1993) J. Gen Virology 74(Pl12):2629–2636; Quintrell et al., (1980) J. Mol. Biol. 143:363–393), as well as its inability to process gag precursor protein in mammalian cells (Vogt et al., (1982) J. Virology 44:725–730) were implied as the possible defects that prevent the synthesis of the virus structural proteins and production of the virus particles.

To determine whether the mammalian cells infected by RCAS-M(4070A) generate virus particles, we infected fresh NIH 3T3 cells with the supernatants of several NIH 3T3/RCAS-M(4070A)NEO clones carrying un-rearranged proviruses. Cells were then subjected to G418 selection. No G418-resistant colonies were detected. This sensitive assay showed that infectious viral particles were not produced by the murine NIH 3T3 cells containing non-rearranged RCAS-M(4070A)NEO provirus. Additionally, this experiment was repeated using RCAS-M2 (4070A)Puro to infect NIH 3T3 cells. Again, no viral particles were detected. Thus, the RSV-based vector RCAS-M(4070A), being inherently replication defective in the mammalian cells, has substantially improved safety features required for sensitive applications such as human gene therapy.

EXAMPLE 5

Construction of RCAS-M2(4070A), A Fast Replicating and Stable Vector

Initially the chimeric virus RCAS-M(4070A) replicates at a considerably lower rate than the parental vector RCASBP (A). Indeed, after transfection of RCAS-M(4070A) into CEFs, 3–4 cell passages were required before detectable amounts of the virus were produced. However, after 5–6 passages on CEFs, the chimeric virus infects these cells efficiently and spreads quickly throughout the entire culture.

To investigate the possibility that genetic changes in the viral genome during this period of initial slow replication permitted the chimeric virus to adapt and grow more efficiently, the env regions of molecular clones of RCAS-M(4070A) provirus containing the neo marker gene (RCAS-M(4070A)NEO) were sequenced.

Cloning of RCAS-M(4070A)NEO Provirus

RCAS-M(4070A)NEO provirus was cloned as follows. Low-molecular-weight DNA was isolated from CEFs infected with RCAS-M(4070A)NEO at passage 3 by the Hirt extraction procedure, Hirt (1967) J. Mol. Bio. 26:365–369. The low-molecular-weight DNA was cleaved with the restriction endonuclease SacI, ligated with SacI-cleaved vector λZAP Express (Stratagene, Calif.) and packaged using GigaPack II Gold packaging extract (Stratagene, Calif.). A library of 4.7×10⁶ independent clones was screened by hybridization with a $^{32}$P-labeled amphotropic env-specific probe (SalI/ClaI fragment derived from pR4070A). Positive phage clones were converted into plasmids by co-infection with ExAssist Helper phage (Stratagene, Calif.). These clones were designated env1, env3, env6, env8, and env9. RCAS-M(4070A)NEO proviral DNA in the resulting plasmid clones was analyzed by cleavage with restriction endonucleases.

Sequencing of the Env Regions of the RCAS-M (4070A)NEO Proviruses

The env gene sequences of the RCAS-M(4070A)NEO provirus clones and the parental plasmid RCAS-M(4070A) NEO were determined by cycle sequencing of both strands using PRISM™ Ready Reaction DyeDeoxy Terminator Cycle Sequencing Kit (Applied Biosystems, CA). Sequencing reactions were analyzed using the Automated 373A DNA Sequencer (Applied Biosystems, CA). The complete sequences of the env genes were assembled using Sequencher software (Gene Codes Corporation, MI).

Figure 8:
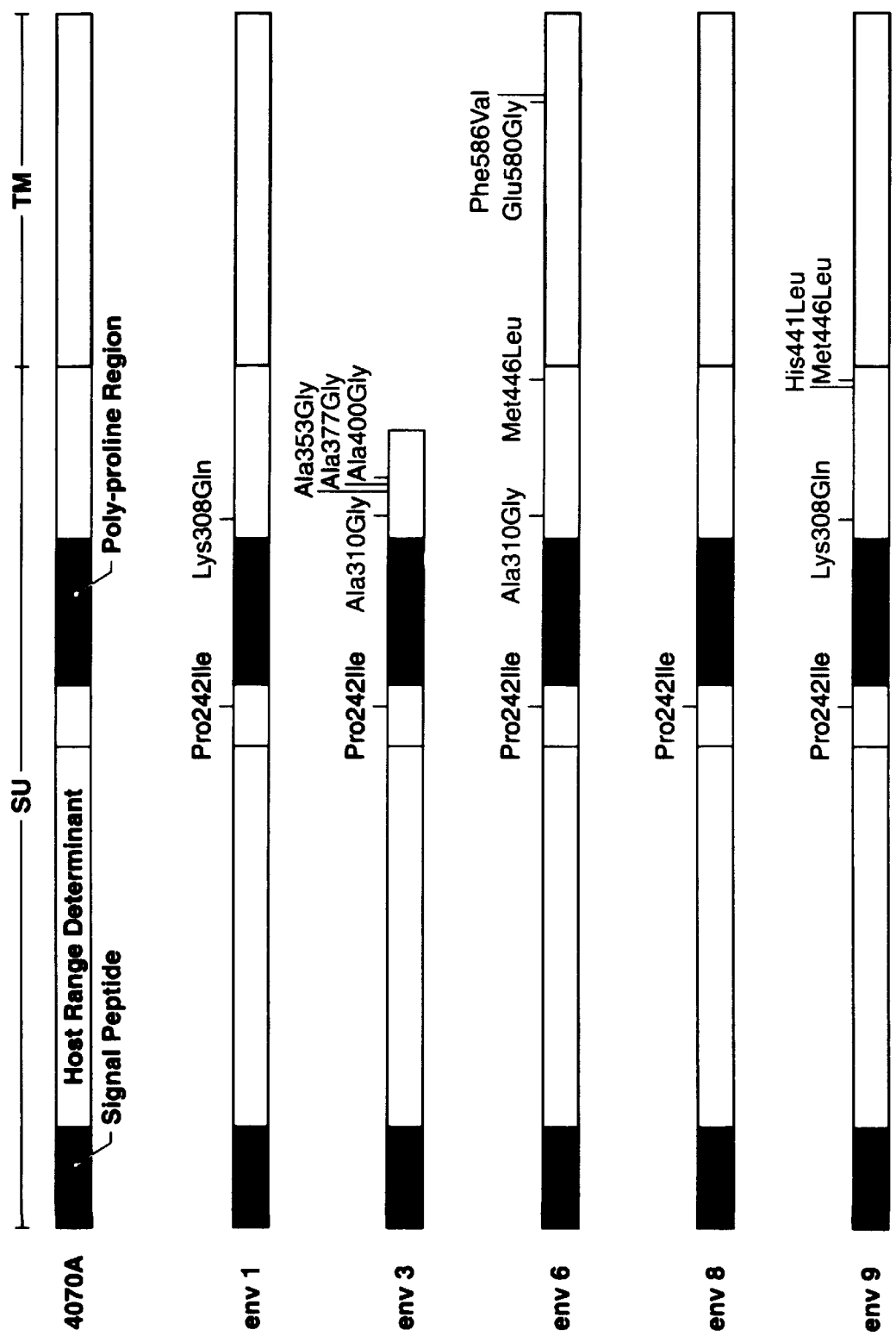

A limited spectrum of mutations in the env region of the individual proviral clones was discovered. The mutations were located primarily in the central and C-terminal regions of the gp70 coding sequence (FIG. 8). In all of the clones, two adjacent cytosines in the region encoding gp70 were mutated to A and T, resulting in the substitution of Ile for Pro at position 242. The same region of the env gene in the parental plasmid RCAS-M(4070A)NEO, had a proline codon at position 242, thus confirming that the Pro242Ile mutation had been selected during the passage of the vector on CEFS, and had not occurred in the course of the vector construction. In addition to this mutation, other substitutions were found, including Lys308Gln (clones env1 and env9), Ala310Gly (clones env3 and env6), and Met446Leu (clones env6 and env9). Some clones had additional amino acid changes, which were seen only in that clone. In addition, in the clone env3, the sequence encoding the C-terminal end of the gp70 and almost all of the p15E was deleted.

The Pro242Ile mutation appears to be critically important for efficient replication, since it is present in all of the clones we derived from passaged RCAS-M(4070A)NEO virus. Furthermore, this mutation alone is sufficient to dramatically increase the efficiency of the virus replication, since it is the only mutation found in the env gene of clone env8, the virus that replicates most efficiently in CEFs and produces the highest titers on mammalian cells.

The replacement of Pro242 with the uncharged isoleucine residue could indicate an important structural change in the gp70, since proline residues are often located at the points of β-turns. This change could reflect the adjustment necessary for the gp70 to recognize both avian and mammalian types of the amphotropic receptor or, alternatively, could enhance the interaction between RSV capsid and the env protein from the amphotropic MLV. It is also possible that the mutation affects the structure and/or function of viral RNA.

The mammalian cellular receptor for amphotropic MLV has recently been cloned and characterized. Miller, et al., (1994) PNAS (USA) 91:78–82; van Zeijl et al., (1994) PNAS (USA) 91:1168–1172. However, the gene for the avian amphotropic receptor has not been unambiguously identified. van Zeijl et al., (1994) PNAS (USA) 91:1168–1172. Passaging of RCAS-M(4070A) through CEFs could select for the viral variants that have increased affinity for the avian amphotropic receptor. No mutations were seen either in the N-terminal half of gp70, the region that appears to determine host range (Ott and Rein (1990) J. Virol 64:757–766; Ott and Rein (1992) J. Virol 66:4632–4638) or in the hypervariable proline-rich region. If the alteration in gp70 increases the affinity of the protein for the avian receptor, it does not compromise the ability of the virus to infect mammalian cells.

Construction of RCAS-M2(4070A)

To construct an "adapted" version of RCAS-M(4070A) which takes advantage of the genetic changes which occurred in the viral genome during the period of initial slow replication, vectors designated RCAS-M2(4070A)Puro1, 6, 8 and 9 were constructed. These vectors contain the (gag-pol)$^{RSV}$-env$^{MLV}$ regions derived from clones env 1, env 6, env 8 and env 9 of RCAS-M(4070A)NEO in place of the (gag-pol)$^{RSV}$-env$^{MLV}$ region of RCAS-M(4070A)Puro.

To construct RCAS-M2(4070A)Puro, DNA fragments containing the (gag-pol)$^{RSV}$-env$^{MLV}$ region were derived from the plasmid clones by digestion with SacI and NotI and ligated with the LTR-Puro-LTR cassette that was obtained by SacI/NotI cleavage of RCAS-MC(4070A)Puro.

The resulting RCAS-M2(4070A)Puro1, 6, 8, and 9 vectors were transfected into CEFs, and the cells were passaged to generate virus. At each passage, the production of viral particles was quantified by determining the virion-associated RT activity, and the number of viruses able to infect mammalian cells was determined by titration on D17 cells as described in Example 2.

Determination of the virion-associated RT activity was performed as described in Whitcomb et al., (1995) J. Virol 69:6228–6238. Briefly, virus particles were recovered from the culture fluid by centrifugation at 14,000 rpm for 30 min at 4° C. Pellets were resuspended in RT buffer (50 mM Tris, pH 8.3, 60 mM NaCl, 12 mM MgCl$_2$, 20 mM dithiothreitol, 0.1% NP-40) containing oligo(dG) (5 μg/ml), poly(rc) (10 μg/ml), dGTP (10 μM) and 10 μCi of [α-$^{32}$P]dGTP (800 Ci/mmol, Amersham, Ill.). Reaction mixtures were incubated at 37° C. for 1 h. Nucleic acids were precipitated by adding 1 ml of 10% trichloracetic acid (TCA), collected on the GF/C glass microfiber filters (Whatman, Oreg.) and washed with 10% TCA and 95% ethanol. Filters were dried and counted in a TriCarb 1500 Liquid Scintillation analyzer (Packard).

Figure 9A:
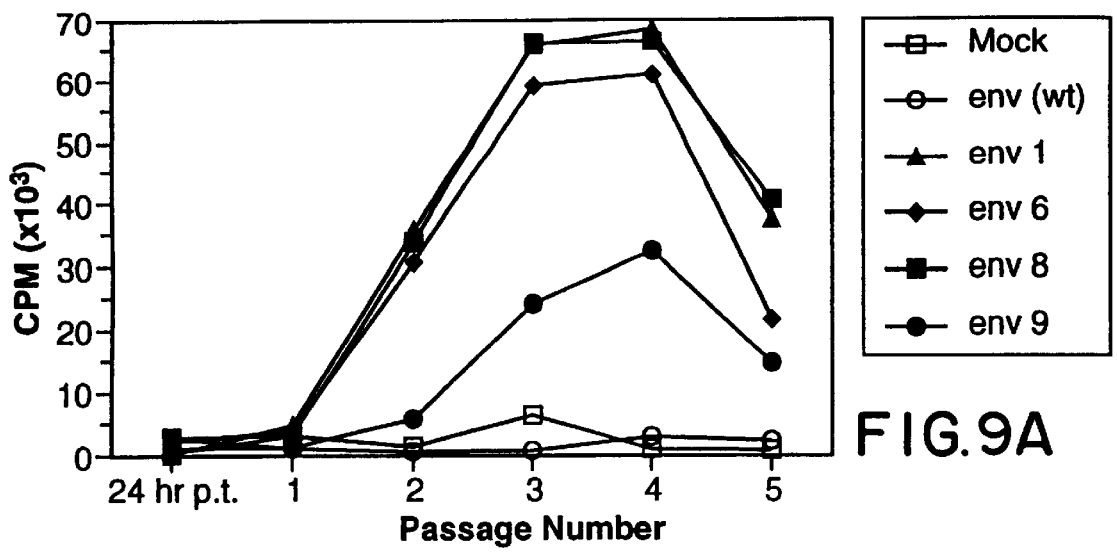
Figure 9B:
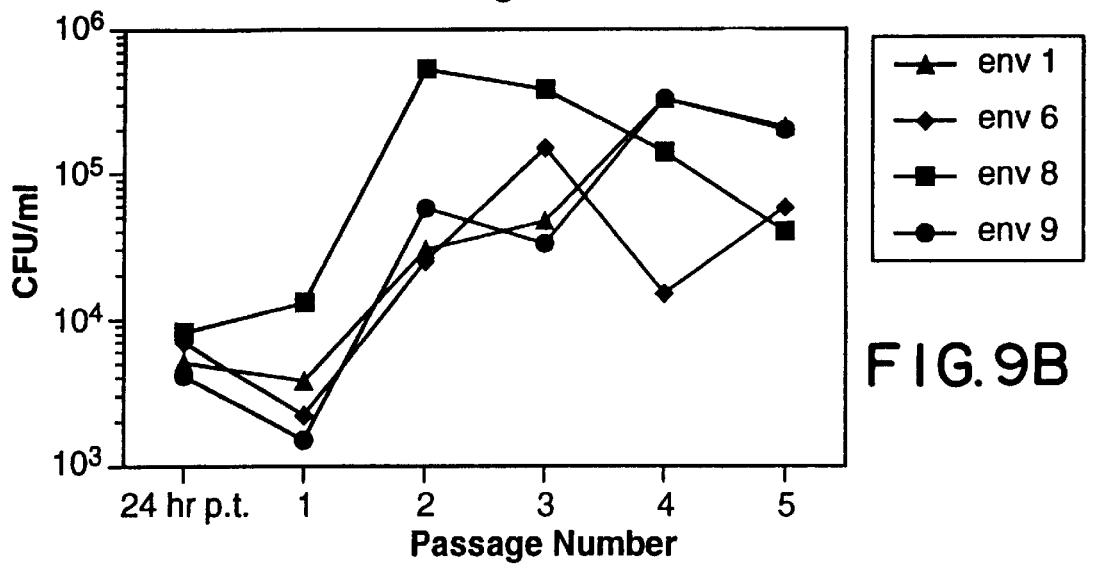

As shown in FIG. 9A, the initial rates of replication of the "adapted" vectors are much faster than the parental vector, RCAS-M(4070A)Puro. Virus production is detectable at passage 1 and reaches a maximum at passages 3–4, which is similar to the initial rates of replication of RCASBP(A). In this experiment, the production of the parental vector, RCAS-M(4070A)Puro, designated "env (wt)," could not be detected until passage 6. The "adapted" RCAS-M2(4070A) Puro vectors are infectious for mammalian cells, exhibiting significant titers on D17 cells (FIG. 9B). The fastest replicating virus (clone env8) reaches the maximum titer on D17 cells by passage 2 (compare FIGS. 9A and B).

Construction of RCAS-M2C(4070A)

Figure 9C:
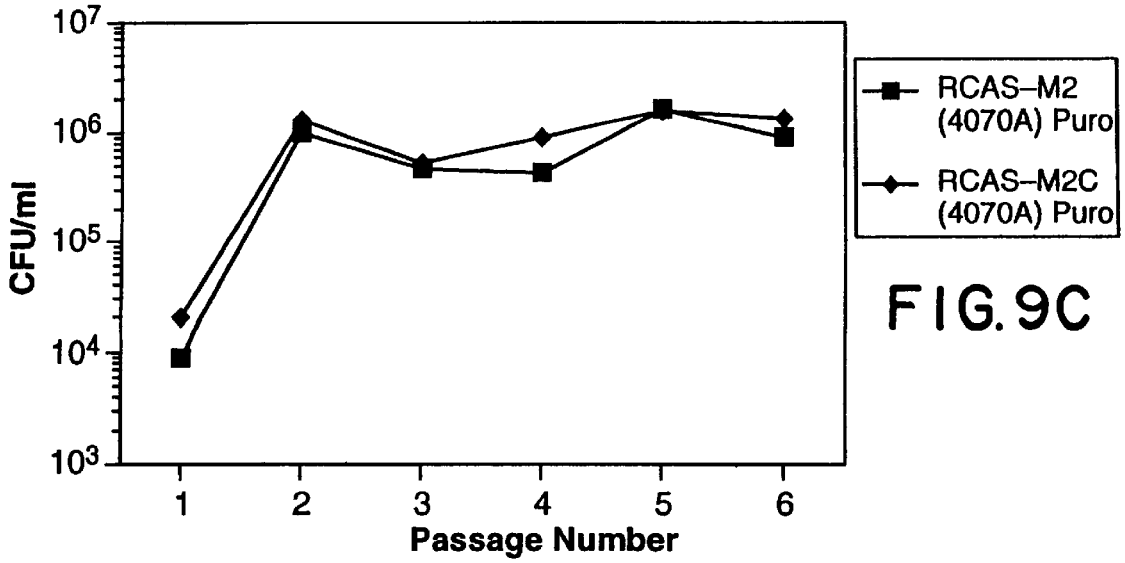

To facilitate cloning into RCAS-M2(4070A), the ClaI site in the env gene of RCAS-M2(4070A)Puro (derived from the clone env8) was eliminated by introducing a silent point mutation by site-directed Mutagenesis as described in the construction of RCAS-MC(4070A) in Example 2. The DNA of the resulting vector RCAS-M2C(4070A)Puro was transfected into CEFs as described in Example 1 and the cells were passaged. At each passage, the number of virus particles able to infect mammalian cells was quantified by titration on D17 cells as described in Example 2. As can be seen in FIG. 9C, the RCAS-M2C(4070A)Puro replicates efficiently in CEFs, and the titer of a virus stock produced at each passage is the same as the titer of the RCAS-M2 (4070A)Puro virus from which it was derived.

In clinical applications of retroviral gene transfer, both the titer and the safety of the vector are of critical importance. The titer of the RCAS-M2C(4070A)Puro vector exceeds $10^6$ cfu/ml. This titer can be obtained by 2–3 cell passages after transfection of CEFs. Not only is the vector simple to use and the titer high, but the vector should also be quite safe. RSV-infected mammalian cells do not produce infectious viral particles and the vector cannot spread in the mammalian host. The inability of RSV to efficiently export a full-length genomic RNA into the cytoplasm (Berberich et al., (1990) *J. Virol* 64:4313–4320; Knight et al., (1993) *J. Gen Virol* 74(Pt 12):2629–2636; Nasioulas et al., (1995) *PNAS* (USA) in press; Quintrell et al., (1980) *J. Mol. Biol.* 143:363–393) as well as its inability to assemble, export, and process the Gag precursor protein in mammalian cells (Nasioulas et al., (1995) *PNAS* (USA) in press, Vogt et al., (1988) *J. Virol* 44:725–730) appear to prevent the production of infectious virus particles. To determine whether the mammalian cells infected by RCAS-M(4070A)NEO generate infectious virus particles, we infected fresh NIH 3T3 cells with the supernatants of several NIH 3T3/RCAS-M (4070A)NEO clones carrying unrearranged proviruses as described in Example 4. Following G418 selection, no G418-resistant colonies were detected, indicating that the mammalian cells infected with RCAS-M(4070A) do not produce infectious particles. No infectious viral particles were detected in the murine NIH 3T3 cells containing non-rearranged RCAS-M(4070A)NEO provirus were detected using G418 selection as described in Example 4. Similar experiments were performed using RCAS-M2 (4070A)Puro to infect the mammalian cells and no virus particles were detected in the infected murine NIH 3T3 cells. Since it is inherently defective in the mammalian cells, the RSV-based vector RCAS-M2C(4070A) appears to have the safety features required for such sensitive applications as human gene therapy. This vector, designated RCAS-M2C (4070A) or RCASBP-M2C (4070A) in this application, was deposited with the American Type Culture Collection, 12301 Parklawn Drive, Rockville, Md. 20852 on Sep. 23, 1998 under ATCC accession number 203326.

For purposes of clarity of understanding, the present invention has been described in some detail by the use of illustration and examples. However, it will be obvious to those skilled in the art that certain modifications may be practiced within the scope of the appended claims.

We claim:

1. An isolated nucleic acid molecule comprising:
   a. at least one long terminal repeat (LTR) isolated from an avian sarcoma leukosis virus (ASLV):
   b. a first nucleic acid sequence selected from a gag region isolated from ASLV:
   c. a second nucleic acid sequence selected from a pol region isolated from an ASLV: and
   d. a third nucleic acid sequence selected from a viral envelope region, said third sequence encoding a protein which binds to both avian and mammalian cells whereby a viral particle harboring said nucleic acid molecule can infect both avian and mammalian cells in titers of at least $10^4$/ml, wherein said viral particle is replication competent in avian cells but is replication defective in mammalian cells.

2. The nucleic acid molecule of claim 1 further comprising at least a fourth nucleic acid sequence.

3. The nucleic acid molecule of claim 1 further comprising a restriction endonuclease site allowing for the insertion of a further nucleic acid sequence.

4. The nucleic acid molecule of claim 1 wherein the LTR, the gag and the pol sequences are isolated from Rous sarcoma virus (RSV).

5. The nucleic acid molecule of claim 1 wherein the envelope sequence is isolated from the amphotropic murine leukemia virus (MLV).

6. The nucleic acid molecule of claim 1 wherein the envelope sequence is a chimeric envelope sequence comprising a sequence encoding the N terminal signal peptide of an ASLV env region and a sequence selected from the coding region of an amphotropic MLV env sequence.

7. The nucleic acid molecule of claim 5 or 6 wherein the envelope sequence contains an isoleucine at position 242.

8. The nucleic acid molecule of claim 7 wherein the envelope sequence is adapted for increased initial replication.

9. The nucleic acid molecule of claim 1 wherein said nucleic acid molecule comprises RCAS-M (4070A) shown in FIG. 3.

10. The nucleic acid molecule of claim 1 wherein said nucleic acid molecule comprises RCAS-M2C(4070A)Puro 8.

11. The nucleic acid molecule of claim 1 wherein said nucleic acid comprises RCAS-M2C(4070A), deposited as ATCC accession no. 203326.

12. A viral particle comprising the nucleic acid molecule of claim 1.

13. A viral particle comprising the nucleic acid molecule of claim 10.

14. A method for inserting at least one nucleic acid sequence of interest into a host cell in vitro comprising introducing the nucleic acid molecule of claim 2 or 10 into the host cell.

15. A method for inserting at least one nucleic acid sequence of interest into a host cell in vitro comprising infecting the host cell with the viral particle of claim 12, wherein the infection of said host cell with said viral particle results in the insertion of a nucleic acid molecule comprised by said viral particle in the host cell.

16. A method for inserting at least one nucleic acid sequence of interest into a host cell in vitro comprising infecting the host cell with the viral particle of claim 13, wherein the infection of said host cell with said viral particle results in the insertion of a nucleic acid molecule comprised by said viral particle in the host cell.

17. An isolated host cell containing the nucleic acid molecule of claim 1.

18. An isolated host cell containing the nucleic acid molecule of claim 10.

* * * * *

SEQUENCE LISTING

<160> NUMBER OF SEQ ID NOS: 6

<210> SEQ ID NO 1
<211> LENGTH: 30
<212> TYPE: DNA
<213> ORGANISM: Unknown Organism
<220> FEATURE:
<223> OTHER INFORMATION: Description of Unknown Organism: NUCLEIC ACIDS
      PROBES

<400> SEQUENCE: 1
aaaagagctc ggccgacacc cagagtggac                                    30

<210> SEQ ID NO 2
<211> LENGTH: 33
<212> TYPE: DNA
<213> ORGANISM: Unknown Organism
<220> FEATURE:
<223> OTHER INFORMATION: Description of Unknown Organism: NUCLEIC ACIDS
      PROBES

<400> SEQUENCE: 2
aaaagagctc tcatggctcg tactctatgg gtt                                33

<210> SEQ ID NO 3
<211> LENGTH: 21
<212> TYPE: DNA
<213> ORGANISM: Unknown Organism
<220> FEATURE:
<223> OTHER INFORMATION: Description of Unknown Organism: NUCLEIC ACIDS
      PROBES

<400> SEQUENCE: 3
ggacgaggtt atgccgctgt g                                             21

-continued

```
<210> SEQ ID NO 4
<211> LENGTH: 46
<212> TYPE: DNA
<213> ORGANISM: Unknown Organism
<220> FEATURE:
<223> OTHER INFORMATION: Description of Unknown Organism: NUCLEIC ACIDS
      PROBES

<400> SEQUENCE: 4
acattaaaga cctgatgggg gctaacatca gctcttaccc ccgtaa            46

<210> SEQ ID NO 5
<211> LENGTH: 23
<212> TYPE: DNA
<213> ORGANISM: Unknown Organism
<220> FEATURE:
<223> OTHER INFORMATION: Description of Unknown Organism: NUCLEIC ACIDS
      PROBES

<400> SEQUENCE: 5
agcccccatc aggtctttaa tgt                                     23

<210> SEQ ID NO 6
<211> LENGTH: 32
<212> TYPE: DNA
<213> ORGANISM: Unknown Organism
<220> FEATURE:
<223> OTHER INFORMATION: Description of Unknown Organism: NUCLEIC ACIDS
      PROBES

<400> SEQUENCE: 6
agcggccgct catggctcgt actctatggg tt                           32
```